United States Patent [19]

Narita et al.

[11] Patent Number: 4,990,508

[45] Date of Patent: Feb. 5, 1991

[54] PYRIDONE CARBOXYLIC ACID DERIVATIVES AND SALTS THEREOF, PROCESS FOR PRODUCING THE SAME AND ANTIBACTERIAL AGENTS COMPRISING THE SAME

[75] Inventors: Hirokazu Narita; Yozo Todo, both of Toyama; Jun Nitta, Toda; Hiroyasu Takagi, Toyama; Fumihiko Iino, Toyama; Mikako Miyajima, Toyma; Yoshikazu Fukuoka, Toyma; Isamu Saikawa, Toyama, all of Japan

[73] Assignee: Toyama Chemical Co., Ltd., Tokyo, Japan

[21] Appl. No.: 337,656

[22] Filed: Apr. 13, 1989

[30] Foreign Application Priority Data

Apr. 23, 1988 [JP] Japan ................................. 63-100628
Mar. 28, 1989 [JP] Japan ................................. 1-75873

[51] Int. Cl.$^5$ .................... A61K 31/54; A61K 31/535; A61K 31/475; C07D 265/34
[52] U.S. Cl. .............................. 514/228.2; 514/230.2; 514/250; 544/32; 544/101; 544/344
[58] Field of Search ................. 544/58.6, 101, 344, 544/32; 514/228.2, 230.2, 250

[56] References Cited

U.S. PATENT DOCUMENTS

| | | | |
|---|---|---|---|
| 3,883,522 | 5/1975 | Gerster | 544/101 |
| 4,539,401 | 9/1985 | Hayakawa et al. | 544/101 |
| 4,540,694 | 9/1985 | Chu | 514/232 |
| 4,603,199 | 7/1986 | Gerster et al. | 544/101 |
| 4,607,032 | 8/1988 | Chu | 514/212 |
| 4,623,650 | 11/1986 | Gilligan et al. | 514/312 |
| 4,762,831 | 8/1988 | Grohe et al. | 544/344 |
| 4,777,253 | 10/1988 | Mitscher et al. | 544/101 |
| 4,882,801 | 4/1989 | Domagala et al. | 514/312 |

FOREIGN PATENT DOCUMENTS

| | | | |
|---|---|---|---|
| 253235 | 3/1968 | European Pat. Off. | 544/101 |
| 284935 | 3/1988 | European Pat. Off. | 544/59 |
| 265230 | 4/1988 | European Pat. Off. | 544/101 |
| 268223 | 5/1988 | European Pat. Off. | 544/101 |
| 270904 | 6/1988 | European Pat. Off. | 544/101 |
| 348088 | 12/1989 | European Pat. Off. | 540/170 |
| 3234529 | 3/1984 | Fed. Rep. of Germany | 544/101 |
| 3522405 | 3/1984 | Fed. Rep. of Germany | 544/101 |
| 3517709 | 10/1986 | Fed. Rep. of Germany | 544/101 |
| 3525108 | 12/1986 | Fed. Rep. of Germany | 544/101 |
| 3543513 | 6/1987 | Fed. Rep. of Germany | 544/101 |
| 3601567 | 7/1987 | Fed. Rep. of Germany . | |
| 3639465 | 5/1988 | Fed. Rep. of Germany | 544/101 |
| 3810080 | 10/1989 | Fed. Rep. of Germany . | |
| 3815481 | 11/1989 | Fed. Rep. of Germany . | |
| 304337 | 9/1987 | Japan | 544/101 |

OTHER PUBLICATIONS

Synthesis 1982, pp. 692–693.
J. Heterocyclic Chem. 24 (1987), pp. 1509–1520.
Chem. Pharm. Bull., vol. 34 (1986), pp. 4088–4102.
J. Chem. Soc. Chem. Commun. 1986, pp. 1308–1311.

*Primary Examiner*—Mukund J. Shah
*Assistant Examiner*—E. C. Ward
*Attorney, Agent, or Firm*—Oblon, Spivak, McClelland, Maier & Neustadt

[57] ABSTRACT

This invention relates to a novel pyridone carboxylic acid derivative having a substituted or unsubstituted cyclopropyl group at the 10-position of pyridobenzoxazine, pyridobenzothiazine or pyridoquinoxaline and a salt thereof, a process for the production thereof and an antibacterial agent comprising the same.

50 Claims, No Drawings

PYRIDONE CARBOXYLIC ACID DERIVATIVES AND SALTS THEREOF, PROCESS FOR PRODUCING THE SAME AND ANTIBACTERIAL AGENTS COMPRISING THE SAME

This invention relates to a novel pyridone carboxylic acid derivative having a substituted or unsubstituted cyclopropyl group at the 10-position of pyridonbenzoxazine, pyridobenzothiazine or pyridoquinoxaline and a salt thereof, a process for producing the same and an antibacterial agent comprising the same.

Ofloxacin has been widely used clinically as a synthetic antibacterial agent of pyridobenzoxazine type. However, it is not completely sufficient in antibacterial activity. It has no satisfactory effect particularly for the treatment of P. aeruginosa infection which is an obstinate disease.

Therefore, it has been desired to develop a synthetic antibacterial agent which is effective for not only Gram-negative bacteria including P. aeruginosa but also Gram-positive bacteria, which shows a broad anti-bacterial spectrum, which has excellent solubility and gives a high blood concentration and which has high safety (e.g. extremely low side effect on the central nervous system).

Under these circumstances, the present inventors have, as a result of extensive research, found that a novel pyridone carboxylic acid derivative and a salt thereof can solve the aforementioned problems.

An object of this invention is to provide a novel pyridone carboxylic acid derivative and a salt thereof having excellent properties, for example, strong antibacterial activities against not only Gram-negative bacteria including P. aeruginosa but also Gram-positive bacteria, particularly against antibiotic resistant bacteria, and giving a high blood concentration when administered orally or parenterally, and having high safety.

Another object of this invention is to provide a process for producing a novel pyridone carboxylic acid derivative and a salt thereof.

A further object of this invention is to provide an antibacterial agent which is useful for the treatment of bacterial infections and which comprises a novel pyridone carboxylic acid derivative or a salt thereof.

Other objects and advantages of this invention will become apparent from the following description.

According to this invention, there is provided a pyridone carboxylic acid derivative represented by the general formula [I] or a salt thereof:

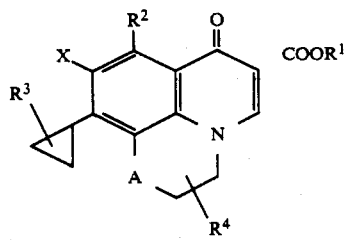

wherein $R^1$ represents a hydrogen atom or a carboxyl-protecting group; $R^2$ represents a hydrogen atom, a halogen atom, an alkoxy group, a protected or unprotected hydroxyl group, a protected or unprotected amino group, a protected or unprotected lower alkylamino group or a di-lower alkylamino group; $R^3$ represents at least one group selected from the group consisting of hydrogen atoms, lower alkyl groups, protected or unprotected amino groups, protected or unprotected lower alkylamino groups, di-lower alkylamino groups, protected or unprotected carboxyl groups, protected or unprotected amino-lower alkyl groups, protected or unprotected lower alkylamino-lower alkyl groups, di-lower alkylamino-lower alkyl groups and protected or unprotected hydroxy-lower alkyl groups; $R^4$ represents at least one group selected from the group consisting of hydrogen atoms, lower alkyl groups, halogeno-lower alkyl groups, protected or unprotected hydroxy-lower alkyl groups, lower alkylidene groups and groups forming a cycloalkane ring with the carbon atom to which $R^4$ bonds; X represents a halogen atom; and A represents an oxygen or sulfur atom or a lower alkyl-substituted or unsubstituted imino group.

In this specification, unless otherwise specified, the term "halogen atom" includes, for example, a fluorine atom, a chlorine atom, a bromine atom and an iodine atom; the term "alkyl group" means a $C_{1-10}$alkyl group such as methyl, ethyl, n-propyl, isopropyl, n-butyl, isobutyl, sec-butyl, tert-butyl, pentyl, hexyl, octyl or the like; the lower alkyl group means a $C_{1-5}$alkyl group of the above-mentioned alkyl groups; the term "alkoxy group" means an —O-alkyl group (the alkyl is a $C_{1-10}$alkyl group); the term "lower alkylamino group" means a $C_{1-5}$alkylamino group such as methylamino, ethylamino, propylamino or the like; the term "di-lower alkylamino group" means a di-$C_{1-5}$alkylamino group such as dimethylamino or the like; the term "amino-lower alkyl group" means an amino-$C_{1-5}$alkyl group such as aminomethyl, aminoethyl, aminopropyl or the like; the term "lower alkylamino-lower alkyl group" means a $C_{1-5}$alkylamino-$C_{1-5}$alkyl group such as methylaminomethyl, methylaminoethyl, ethylaminomethyl, methylaminopropyl, propylaminoethyl or the like; the term "di-lower alkylamino-lower alkyl group" means a di-$C_{1-5}$alkylamino-$C_{1-5}$alkyl group such as dimethylaminomethyl, diethylaminomethyl, diethylaminoethyl, dimethylaminopropyl or the like; the term "hydroxy-lower alkyl group" means a hydroxy-$C_{1-5}$alkyl group such as hydroxymethyl, hydroxyethyl, hydroxypropyl or the like; the term "halogeno-lower alkyl group" means a halogeno-$C_{1-5}$alkyl group such as chloromethyl, bromomethyl, dichloromethyl, trichloromethyl, chloroethyl, dichloroethyl, trichloroethyl, chloropropyl or the like; the term "lower alkylidene group" means a $C_{1-5}$alkylidene group such as methylene, ethylidene, propylidene, isopropylidene or the like; and the term "cycloalkane ring" means a $C_{3-6}$cycloalkane ring such as cyclopropane, cyclobutane, cyclopentane, cyclohexane or the like.

This invention will be explained in detail below.

In the compound represented by the general formula [I] or a salt thereof, the carboxyl-protecting group for $R^1$ and $R^3$ includes, for example, ester-forming groups which may be removed by catalytic reduction, chemical reduction or other treatments under mild conditions; ester-forming groups which may be easily removed in a living body; organic silyl-containing groups, organic phosphorus-containing groups and organic tin-containing groups which may be easily removed by treatment with water or an alcohol; and other various well-known ester-forming groups as described in Japanese Patent Application Kokai (Laid-Open) No. 80,665/84.

In the definitions of $R^2$ and $R^3$, the protecting groups for amino groups, lower alkylamino groups, amino-lower alkyl groups and lower alkylamino-lower alkyl groups include those conventionally used in the art, such as formyl, acetyl, benzyl and other conventional amino-protecting groups as described in Japanese Patent Application Kokai (Laid-Open) No. 80,665/84.

In the definitions of $R^2$, $R^3$ and $R^4$, the protecting groups for hydroxyl groups and hydroxy-lower alkyl groups include those conventionally used in the art, for example, conventional hydroxyl-protecting groups as described in Japanese Patent Application Kokai (Laid-Open) No. 80,665/84, such as an organic silyl group which can easily be removed by a treatment with water or an alcohol, a formyl group, an acetyl group, a benzyl group and the like.

The salt of the compound represented by the general formula [I] includes conventional salts at basic groups such as an amino group and the like, and at acidic groups such as a hydroxyl group, a carboxyl group and the like. The salts at the basic groups include, for example, salts with mineral acids such as hydrochloric acid, hydrobromic acid, sulfuric acid and the like; salts with organic carboxylic acids such as tartaric acid, formic acid, citric acid, trichloroacetic acid, trifluoroacetic acid and the like; salts with sulfonic acids such as methanesulfonic acid, benzenesulfonic acid, p-toluenesulfonic acid, mesitylenesulfonic acid, naphthalenesulfonic acid and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-8-phenethylamine, 1-ephenamine, N,N'-dibenzylethylenediamine and the like.

If the compound represented by the general formula [I] and a salt thereof have isomers (for example, optical isomers, geometrical isomers, tautomers and the like), this invention includes all of the isomers, crystal forms, solvates and hydrates thereof The antibacterial activities and acute toxicities of typical compounds of this invention are shown below.

hours, after which the growth of the bacteria was observed, to determine the minimum concentration at which the growth of the bacteria was inhibited as MIC ($\mu$g/ml). The amount of the inoculated bacteria was $10^4$ cells/plate ($10^6$ cells/ml). The MIC values of the following test compounds are as shown in Table 1.

The asterisk in Table 1 means $\beta$-Lactamase-producing bacteria.

Test compounds:
1. 10-(1-Aminocyclopropyl)-9-fluoro-3-methyl-7-oxo-2,3-dihydro-7H-pyrido[1,2,3-de][1,4] benzoxazine-6carboxylic acid hydrochloride
2. 8-Amino-10-(1-aminocyclopropyl)-9-fluoro-3-methyl-7-oxo-2,3-dihydro-7H-pyrido[1,2,3-de][1,4]-benzoxazine-6-carboxylic acid hydrochloride
3. 10-(1-Aminocyclopropyl)-8,9-difluoro-3-methyl-7-oxo-2,3-dihydro-7H-pyrido[1,2,3-de][1,4]benzoxazine-6-carboxylic acid hydrochloride
4. 10-(1-Aminocyclopropyl)-9-fluoro-8-hydroxy-3-methyl-7-oxo-2,3-dihydro-7H-pyrido[1,2,3-de][1,4]-benzoxazine-6-carboxylic acid hydrochloride
5. (S)-10-(1-aminocyclopropyl)-9-fluoro-3-methyl-7-oxo-2,3-dihydro-7H-pyrido[1,2,3-de][1,4]benzoxazine-6-carboxylic acid hydrochloride
6. 10-(1-Aminocyclopropyl)-9-fluoro-3-fluoromethyl-7-oxo-2,3-dihydro-7H-pyrido[1,2,3-de][1,4]benzoxazine-6-carboxylic acid hydrochloride
7. (S)-10-(1-aminocyclopropyl)-3-ethyl-9-fluoro-7-oxo-2,3-dihydro-7H-pyrido[1,2,3-de][1,4]benzoxazine-6carboxylic acid hydrochloride
8. 10-(1-Aminocyclopropyl)-9-fluoro-3-methylene-7-oxo-2,3-dihydro-7H-pyrido[1,2,3-de][1,4]benzoxazine-6-carboxylic acid hydrobromide
9. 10'-(1-Aminocyclopropyl)-9'-fluoro-7+-oxospiro{cyclopropane-1,3'(2'H)-[7H]-pyrido[1,2,3-de][1,4]benzoxazine}-6'-carboxylic acid hydrochloride
10. (S)-10-(1-amino-2-methylcyclopropyl)-9-fluoro-3-methyl-7-oxo-2,3-dihydro-7H-pyrido[1,2,3-de][1,4]-benzoxazine-6-carboxylic acid hydrochloride
11. (S)-10-[1-(N-methylamino)cyclopropyl]-9-fluoro-3-methyl-7-oxo-2,3-dihydro-7H-pyrido[1,2,3-de][1,4]-benzoxazine-6-carboxylic acid hydrochloride Control compound (ofloxacin):
($\pm$)9-Fluoro-2,3-dihydro-3-methyl-10-(4-methyl-1-piperazinyl)-7-oxo-7H-pyrido[1,2,3-de][1,4]benzoxazine-6carboxylic acid

TABLE 1

| Bacteria | MIC ($\mu$g/ml) Test Compound No. | | | | | | | | | | | Control compd. |
|---|---|---|---|---|---|---|---|---|---|---|---|---|
| | 1 | 2 | 3 | 4 | 5 | 6 | 7 | 8 | 9 | 10 | 11 | |
| E. coli NIHJ | ≦0.05 | ≦0.05 | ≦0.05 | ≦0.05 | ≦0.05 | ≦0.05 | ≦0.05 | 0.1 | 0.1 | ≦0.05 | ≦0.05 | ≦0.05 |
| E. coli TK-111 | ≦0.05 | ≦0.05 | ≦0.05 | ≦0.05 | ≦0.05 | ≦0.05 | ≦0.05 | ≦0.05 | ≦0.05 | ≦0.05 | ≦0.05 | ≦0.05 |
| K. pneumoniae Y-4* | 0.2 | 0.39 | 0.39 | 0.39 | ≦0.05 | 0.2 | 0.2 | 0.2 | 0.39 | 0.2 | 0.1 | 0.39 |
| S. marcescens W-134 | 0.1 | 0.2 | 0.2 | 0.2 | ≦0.05 | 0.1 | 0.1 | 0.2 | 0.2 | 0.1 | 0.1 | 0.2 |
| P. mirabilis T-111 | 0.1 | 0.39 | 0.2 | 0.2 | ≦0.05 | 0.1 | 0.2 | 0.39 | 0.39 | 0.2 | 0.1 | 0.39 |
| M. morganii T-216 | ≦0.05 | 0.1 | ≦0.05 | ≦0.05 | ≦0.05 | ≦0.05 | ≦0.05 | 0.1 | 0.1 | ≦0.05 | ≦0.05 | 0.1 |
| C. freundii N-7 | ≦0.05 | 0.1 | 0.2 | 0.39 | ≦0.05 | 0.1 | 0.1 | 0.1 | 0.2 | ≦0.05 | 0.1 | 0.39 |
| P. aeruginosa GN-918* | 0.2 | 0.78 | 0.78 | 0.78 | 0.1 | 0.2 | 0.2 | 0.39 | 0.39 | 0.2 | 0.2 | 3.13 |

1. Antibacterial activity

Test method

According to the standard method of Japan Society of Chemotherapy [CHEMOTHERAPY, 29 (1), 76–79 (1981)], a bacteria solution obtained by culturing in Heart Infusion broth (manufactured by Eiken Kagaku) at 37° C. for 20 hours was inoculated onto a Heart Infusion agar containing a drug and cultured at 37° C. for 20

2. Acute toxicity

A test compound was intravenously administered to a group of three ICR strain male mice each weighing 22±1 g to investigate the acute toxicity.

The test compound was dissolved in a 0.1N aqueous sodium hydroxide solution, and the resulting solution was applied.

As a result, the 50% lethal dosage (LD$_{50}$) of the test compound No. 5 was >1,000 mg/kg.

The process for producing the compound of this invention will be explained below.

The compound of this invention can be produced, for example, according to the following production route:

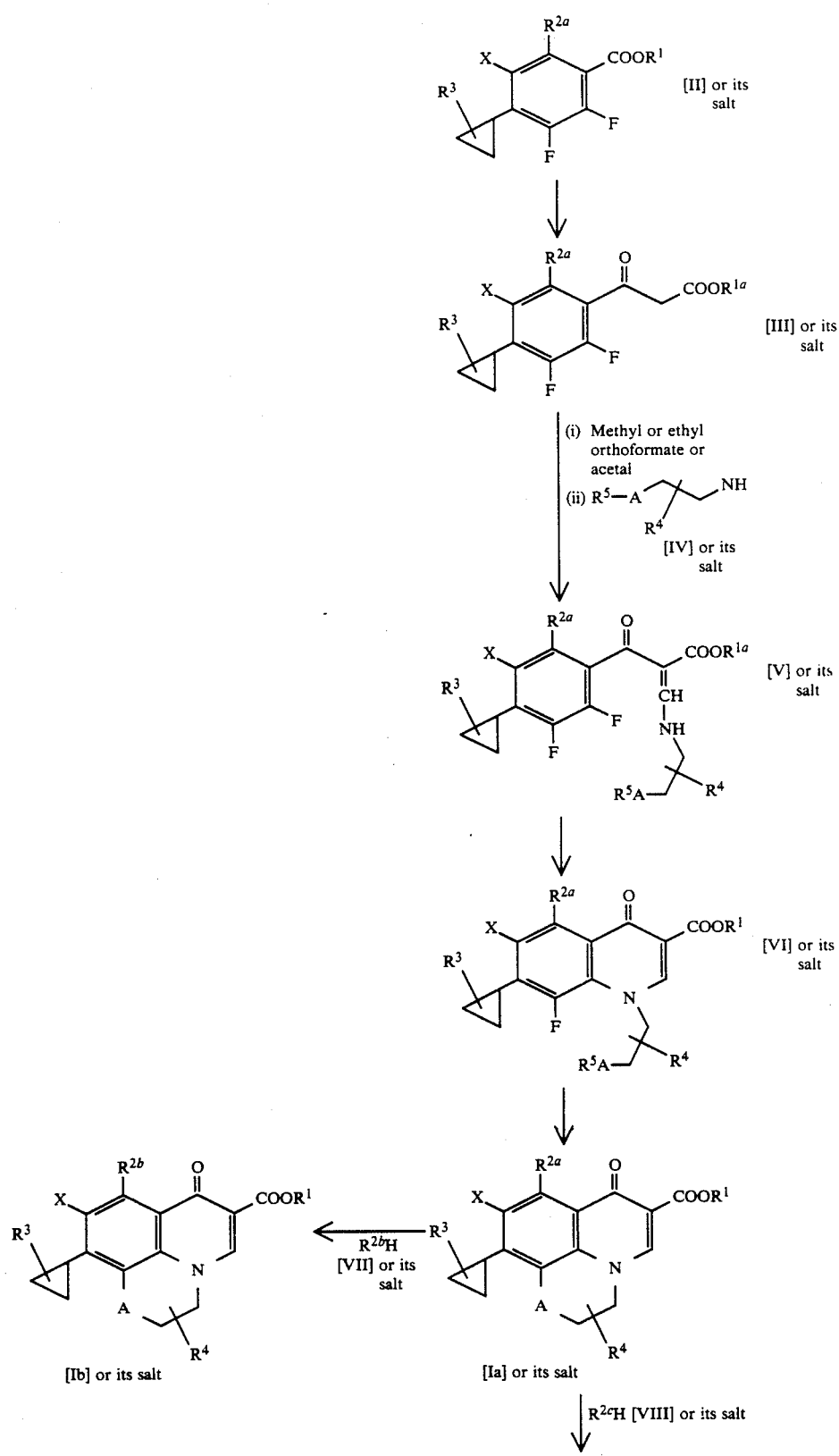

-continued

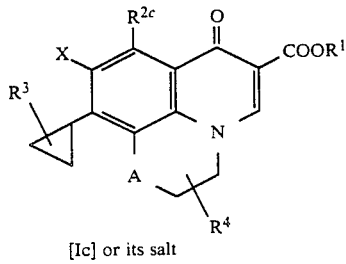

[Ic] or its salt wherein $R^1$, $R^3$, $R^4$, A and X have the same meanings as defined above; $R^{1a}$ represents the same carboxyl-protecting group as in the definition of $R^1$; $R^{2a}$ represents a hydrogen atom or the same halogen atom as in the definition of $R^2$; $R^{2b}$ represents the same alkoxy group or protected or unprotected hydroxyl group as in the definition of $R^2$; $R^{2c}$ represents the same protected or unprotected amino group, protected or unprotected lower alkylamino group or di-lower alkylamino group as in the definition of $R^2$; and $R^5$ represents a hydrogen atom or the same amino-protecting group as in the definitions of $R^2$ and $R^3$.

The salts of the compounds of the general formulas [II], [III], [IV], [V], [VI], [VII], [VIII], [Ia], [Ib] and [Ic] include the same salts as those of the compounds of the general formula [I].

Each step of the above production route is explained below.

(1) A compound of the general formula [III] or a salt thereof can be obtained by subjecting a compound of the general formula [II] or a salt thereof to a keto-esterification reaction conventionally known in the art.

(i) For example, the carboxyl group of a compound of the general formula [II] or a salt thereof is converted to an acid halide with a halogenating agent such as thionyl chloride or the like; then the acid halide is reacted with a metal salt (e.g. sodium salt or ethoxy-magnesium salt) of a malonic acid diester; and thereafter the resulting product is subjected to partial removal of carboxyl-protecting group and decarboxylation with p-toluene sulfonic acid in a hydrous solvent or with trifluoroacetic acid, to obtain a compound of the general formula [III] or a salt thereof.

The solvent to be used in the reaction between the acid halide and the metal salt of a malonic acid diester may be any solvent as long as it has no adverse effect on the reaction, and it includes, for example, aromatic hydrocarbons such as benzene, toluene, xylene and the like; ethers such as dioxane, tetrahydrofuran, diethyl ether and the like; halogenated hydrocarbons such as methylene chloride, chloroform, dichloroethane and the like; and amides such as N,N-dimethylformamide, N,N-dimethylacetamide and the like. These solvents may be used alone or in admixture of two or more.

The amount of the metal salt of a malonic acid diester to be used is at least one mole, preferably 1–3 moles, per mole of the acid halide of the compound of the general formula [II].

This reaction may usually be carried out at $-50°$ C. to $100°$ C. for 5 minutes to 30 hours.

(ii) Alternatively, the compound of the general formula [III] or a salt thereof can be obtained in accordance with, for example, the method described in Angew. Chem. Int. Ed. Engl. Vol. 18, p. 72, (1979). That is, the carboxyl group of a compound of the general formula [II] or a salt thereof is converted to an active acid amide with, for example, N,N'-carbonyldiimidazole; and the active acid amide is reacted with a magnesium salt of a malonic acid monoester to obtain a compound of the general formula [III] or a salt thereof.

The solvent to be used in the reaction between the active acid amide and the magnesium salt of a malonic acid monoester may be any solvent as long as it has no adverse effect on the reaction. It includes specifically the same solvents as mentioned in (1)(i) above.

The amount of N,N'-carbonyldiimidazole to be used and the amount of the magnesium salt of a malonic acid monoester to be used are each at least one mole, preferably 1–2 moles, per mole of the compound of the general formula [II] or a salt thereof.

This reaction may usually be carried out at $0°$–$100°$ C., preferably $10°$–$80°$ C., for 5 minutes to 30 hours.

(2)(i) A compound of the general formula [V] or a salt thereof can be obtained by reacting the compound of the general formula [III] or a salt thereof with methyl or ethyl orthoformate in acetic anhydride and then reacting the resulting product with a compound of the general formula [IV] or a salt thereof. (In this case, if an optically active compound of the general formula [IV] or a salt thereof is used, there can be obtained an optically active pyridone carboxylic acid derivative of the general formula [I].)

The solvent to be used in this reaction may be any solvent as long as it has no adverse effect on the reaction, and it includes, for example, aromatic hydrocarbons such as benzene, toluene, xylene and the like; ethers such as dioxane, tetrahydrofuran, anisole, diethylene glycol diethyl ether, dimethyl Cellosolve and the like; alcohols such as methanol, ethanol, propanol and the like; halogenated hydrocarbons such as methylene chloride, chloroform, dichloroethane and the like; amides such as N,N-dimethylformamide, N,N-dimethylacetamide and the like: and sulfoxides such as dimethyl sulfoxide and the like. These solvents can be used alone or in admixture of two or more.

The amount of methyl or ethyl orthoformate used is at least one mole, preferably about 1–10 moles, per mole of the compound of the general formula [III] or a salt thereof. This reaction may usually be carried out at $0°$–$150°$ C., preferably $50°$–$150°$ C., for 20 minutes to 50 hours.

In the subsequent reaction with the compound of the general formula [IV] or a salt thereof, said compound or a salt thereof is used in an amount of at least one mole per mole of the compound of the general formula [III] or a salt thereof, and the reaction may usually be carried out at $0°$–$100°$ C., preferably $10°$–$60°$ C., for 20 minutes to 30 hours.

(2)(ii) Alternatively, the compound of the general formula [V] or a salt thereof can be obtained by reacting the compound of the general formula [III] or a salt thereof with an acetal such as N,N-dimethylformamidedimethyl acetal, N,N-dimethylformamidediethyl acetal or the like and then reacting the resulting product with the compound of the general formula [IV] or a salt thereof. (In this case, if an optically active compound of the general formula [IV] or a salt thereof is used, there can be obtained an optically active pyridone carboxylic acid derivative of the general formula [I].)

The solvent to be used in this reaction may be any solvent as long as it has no adverse effect on the reaction. It includes, for example, the same solvents as mentioned in (2)(i) above.

The amount of the acetal to be used is at least one mole, preferably about 1.0–5.0 moles, per mole of the compound of the general formula [III] or a salt thereof.

This reaction may usually be carried out at 0°–100° C., preferably 50°–85° C., for 20 minutes to 50 hours.

In the subsequent reaction with the compound of the general formula [IV] or a salt thereof, said compound or a salt thereof is used in an amount of at least one mole per mole of the compound of the general formula [III] or a salt thereof, and the reaction may usually be carried out at 0°–100° C., preferably 10°–60° C., for 20 minutes to 30 hours.

(3) A compound of the general formula [VI] or a salt thereof can be obtained by subjecting the compound of the general formula [V] or a salt thereof to a ring-closure reaction in the presence or absence of a metal fluoride or a base.

The solvent to be used in this reaction may be any solvent as long as it has no adverse effect on the reaction. It includes, for example, amides such as N,N-dimethylformamide, N,N-dimethylacetamide and the like; ethers such as dioxane, anisole, diethylene glycol dimethyl ether, dimethyl Cellosolve and the like; and solfoxides such as dimethyl sulfoxide and the like. These solvents may be used alone or in admixture of two or more.

The metal fluoride to be optionally used in this reaction includes, for example, sodium fluoride, potassium fluoride and the like. The base to be optionally used includes, for example, sodium hydrogencarbonate, potassium carbonate, potassium tert-butoxide, sodium hydride and the like. The amount of the metal fluoride or base to be used is at least one mole, preferably 1.0–1.5 moles, per mole of the compound of the general formula [V] or a salt thereof.

This reaction may usually be carried out at 0°–180° C. for 5 minutes to 30 hours.

(4)(i) A compound of the general formula [Ia] or a salt thereof can be obtained by subjecting the compound of the general formula [VI] or a salt thereof to a ring-closure reaction in the presence or absence of a metal fluoride or a base.

This reaction may be carried out under the same conditions as mentioned in (3) above.

(4)(ii) Alternatively, the compound of the general formula [Ia] or a salt thereof can be obtained by subjecting the compound of the general formula [V] or a salt thereof to a ring-closure reaction in the presence or absence of a metal fluoride or a base.

The amount of the metal fluoride or base to be used is at least two moles per mole of the compound of the general formula [V] or a salt thereof.

This reaction may usually be carried out at 0°–180° C. for 5 minutes to 30 hours.

(5) A compound of the general formula [Ib] or a salt thereof can be obtained by reacting the compound of the general formula [Ia] wherein $R^{2a}$ is a halogen atom, or a salt thereof with an alcohol of the general formula [VII] or a salt thereof in the presence or absence of a base.

The solvent to be used in this reaction may be any solvent as long as it has no adverse effect on the reaction. It includes, for example, aromatic hydrocarbons such as benzene, toluene, xylene and the like; ethers such as dioxane, tetrahydrofuran, diethyl ether and the like; halogenated hydrocarbons such as methylene chloride, chloroform, dichloroethane and the like; nitriles such as acetonitrile and the like; and amides such as N,N-dimethylformamide, N,N-dimethylacetamide and the like. These solvents may be used alone or in admixture of two or more.

The base to be optionally used in this reaction includes, for example, sodium, potassium, potassium tert-butoxide, sodium hydride and the like.

The amount of the alcohol of the general formula [VII] or a salt thereof to be used and the amount of the base to be optionally used are each at least one mole per mole of the compound of the general formula [Ia] wherein $R^{2a}$ is a halogen atom, or a salt thereof.

This reaction may usually be carried out at 0°–150° C. for 10 minutes to 20 hours. (6) A compound of the general formula [Ic] or a salt thereof can be obtained by reacting the compound of the general formula [Ia] wherein $R^{2a}$ is a halogen atom, or a salt thereof with an amine of the general formula [VIII] or a salt thereof in the presence or absence of a base.

The solvent to be used in this reaction may be any solvent as long as it has no adverse effect on the reaction. It includes, for example, the same solvents as mentioned in (5) above.

The base to be optionally used in this reaction includes, for example, organic or inorganic bases such as triethylamine, diisopropylethylamine, 1,8-diazabicyclo[5.4.0]undec-7-ene (DBU), pyridine, potassium tert-butoxide, potassium carbonate, sodium carbonate, sodium hydride and the like.

The amount of the amine of the general formula [VIII] or a salt thereof to be used is preferably 2–10 moles per mole of the compound of the general formula [Ia] or a salt thereof. The amount of the amine of the general formula (VIII) or a salt thereof can be reduced by appropriately using a base.

This reaction may usually be carried out at 0°–150° C., preferably 15°–100° C., for 5 minutes to 30 hours.

The compound of the general formula [I] or a salt thereof can be converted to another compound of the general formula [I] or a salt thereof in a manner known per se, such as oxidation, reduction, rearrangement, substitution, halogenation, dehydration, hydrolysis or the like, or an appropriate combination thereof.

Of the compounds of the general formulas [II], [III], [IV], [V], [VI], [VII] and [VIII], those having an amino group, a hydroxyl group or a carboxyl group can be obtained by previously protecting said group with a conventional protecting group, and, after the reaction, removing the protecting group in a manner known per se.

The compound of the general formula [II] or a salt thereof to be used as the starting material in production of the compound of this invention is a novel compound and can be produced according to, for example, the following production route:

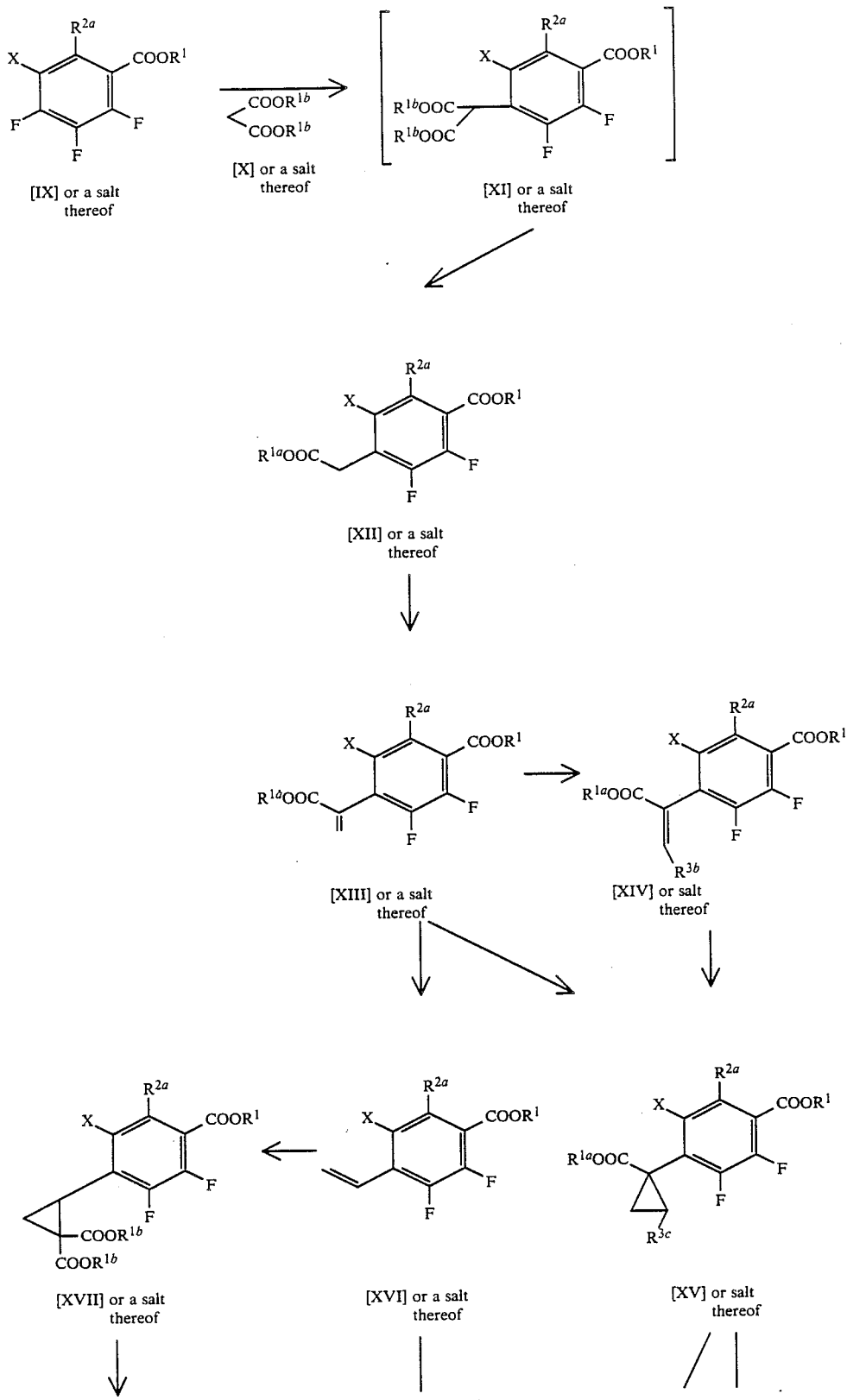

-continued

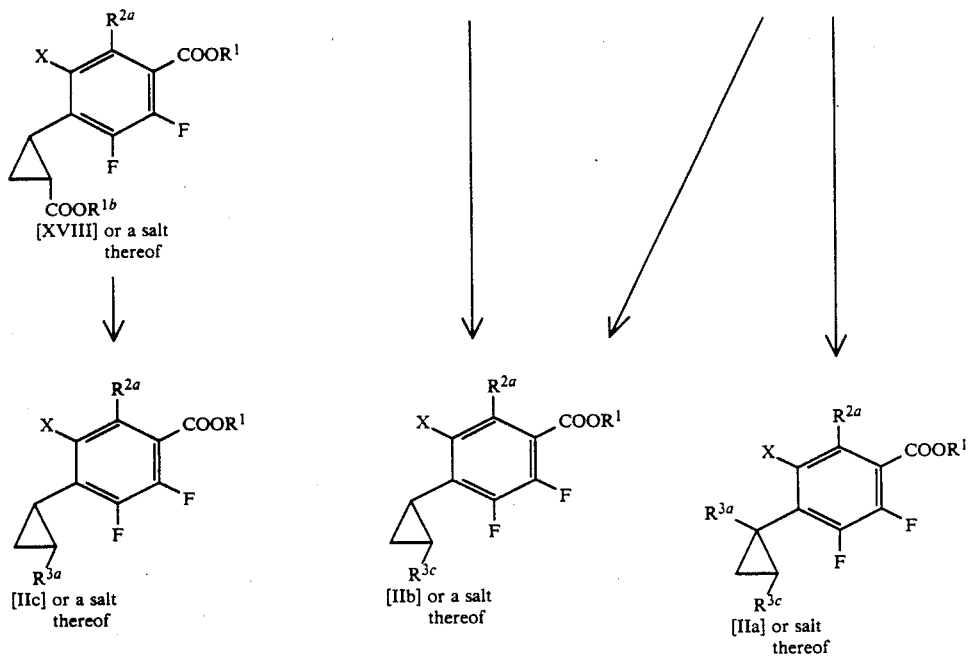

In the above production route, $R^1$, $R^{1a}$, and X have the same meanings as defined above; Rlb represents the same carboxyl-protecting group as in the definition of $R^1$; $R^{3a}$ represents a hydrogen atom or the same protected or unprotected amino group, protected or unprotected lower alkylamino group, di-lower alkylamino group, protected or unprotected amino-lower alkyl group, protected or unprotected lower alkylamino-lower alkyl group, di-lower alkylamino-lower alkyl group or protected or unprotected hydroxy-lower alkyl group as in the definition of $R^3$; $R^{3b}$ represents the same lower alkyl group as in the definition of $R^3$; and $R^{3c}$ represents a hydrogen atom or the same lower alkyl group as in the definition of $R^3$.

In each of the compounds of the general formulas [X] and [XI] and salts thereof, two $R^{1b}$s may be the same or different.

The salts of the compounds of the general formulas [IX], [XI], [XII], [XIII], [XIV], [XV], [XVI], [XVII], [XVIII], [IIa], [IIb] and [IIc] include the same salts as those of the compound of the general formula [I].

The salts at the active methylene of the compounds of the general formulas [X] and [XII] include salts with alkali metals such as sodium, potassium, lithium and the like.

A compound of the general formula [XII] or a salt thereof can be obtained by reacting a compound of the general formula [IX] or a salt thereof with a compound of the general formula [X] or a salt thereof in accordance with the method as described in U.S. Pat. No. 3,590,036 to convert it into a compound of the general formula [XI] or a salt thereof; then subjecting this compound or a salt thereof to removal of protecting group and decarboxylation reaction according to a conventional method; and thereafter introducting a carboxyl-protecting group into the resulting product.

The compound of the general formula [XII] or a salt thereof can be converted into a compound of the general formula [XIII] or a salt thereof according to the method as described in Chem. Ber. Vol. 99, p. 2407 (1966).

The compound of the general formula [XIII] or a salt thereof can be converted into a compound of the general formula [XIV] or a salt thereof by reacting the former with a diazoalkane.

A compound of the general formula [IIb] or a salt thereof can be obtained by subjecting the compound of the general formula [XIII] or a salt thereof to removal of protecting group and decarboxylation reaction according to a conventional method to convert it into a compound of the general formula [XVI] or a salt thereof and then subjecting said compound or a salt thereof to a 1,3-dipolar addition reaction with a diazoalkane and further to denitrogenation by heating.

Alternatively, the compound of the general formula [IIb] or a salt thereof can be obtained by reacting the compound of the general formula [XIII] or a salt thereof or the compound of the general formula [XIV] or a salt thereof with trimethylsulfoxonium iodide in the presence of a base such as sodium hydride or the like to convert it into a compound of the general formula [XV] or a salt thereof and then subjecting said compound or a salt thereof to removal of protecting group and decarboxylation by a conventional method.

A compound of the general formula [IIa] or a salt thereof can be obtained by subjecting a compound of the general formula [XV] or a salt thereof to a known reaction such as removal of protecting group, reduction, amination, Curtius reaction, alkylation or the like.

A compound of the general formula [XVIII] or a salt thereof can be obtained by subjecting the compound of the general formula [XVI] or a salt thereof to bromination or chlorination, thereafter reacting the resulting product with a base such as 1,8-diazabicyclo[5,4,0]undec-7-ene-(DBU) and the like and then reacting the resulting product with a compound of the general formula [X] or a salt thereof to convert it into a compound of the general formula [XVII] or a salt thereof, and subsequently subjecting said compound or a salt thereof to removal of protecting group and decarboxylation by a conventional method to convert it into a compound of the general formula [XVIII] or a salt thereof. A compound of the general formula [IIc] or a salt thereof can be obtained by further subjecting the compound of the general formula [XVIII] or a salt thereof to a known reaction such as removal of protecting group reduction, amidation, Curtius reaction, alkylation or the like or to an appropriate combination thereof.

Of the compounds of the general formulas [IX], [XI], [XII], [XIII], [XIV], [XV], [XVI], [XVII] and [XVIII], those having an amino, hydroxyl or carboxyl group can be obtained by previously protecting said group with a conventional protecting group and, after the reaction, removing the protecting group in a manner known per se.

The compound of the general formula [I] or a salt thereof obtained above can be isolated and purified according to conventional methods such as extraction, crystallization, column chromatography and the like.

When the compound of this invention is used as a drug or medicine, it is appropriately combined with carriers which are used in conventional pharmaceutical preparations, and is prepared into tablets, capsules, powders, syrups, granules, suppositories, ointments, injections and the like in a conventional manner. The administration routes, dosage and number of administrations can be appropriately varied depending upon the symptoms of patients, and it may be usually administered orally or parenterally (for example, by injection, drip infusion, rectal administration) to an adult in an amount of 0.1 to 100 mg/kg/day in one to several portions.

This invention is explained in more detail below referring to Reference Examples, Examples and Preparation Examples. However, this invention is not restricted to these Examples.

In the Examples, the mixing ratio if mixed solvent is by volume in all cases. As the carrier in column chromatography, there was used a silica gel (Kieselgel 60, Art. 7734 manufactured by Merck Co.).

The following abbreviations are used in the Examples:
Me: methyl,
Et: ethyl,
Boc: tert-butoxycarbonyl,
Z: benzyloxycarbonyl,
THP: 2-tetrahydropyranyl,
+ : tert-butyl,
TFA: trifluoroacetic acid,
DMSO: N,N-dimethylsulfoxide,
D$_2$O: heavy water.

REFERENCE EXAMPLE 1

In 500 ml of N,N-dimethylformamide was suspended 10.2 g of 60% sodium hydride. Thereinto was dropped 55.0 g of di-tert-butyl malonate in 1 hour with ice-cooling. The resulting mixture was stirred for 10 minutes at the same temperature. Thereto was added 48.0 g of methyl pentafluorbenzoate. The resulting mixture was stirred for 2 hours at room temperature. The reaction mixture was added to a mixture of 1 liter of water and 400 ml of ethyl acetate. The resulting mixture was adjusted to pH 3 with 6N hydrochloric acid. The organic layer was separated, washed with water and a saturated aqueous sodium chloride solution in this order, and dried over anhydrous magnesium sulfate. The solvent was removed by distillation under reduced pressure. The residue obtained was dissolved in 150 ml of trifluoroacetic acid. The resulting solution was stirred at room temperature for 20 hours. The reaction mixture was concentrated under reduced pressure. To the residue obtained were added 200 ml of diethyl ether and 600 ml of water in this order. The organic layer was separated, washed with water and a saturated aqueous sodium chloride solution in this order, and dried over anhydrous magnesium sulfate. The solvent was removed by distillation under reduced pressure. To the residue obtained was added 50 ml of toluene. The resulting mixture was refluxed for 1.5 hours. The reaction mixture was concentrated under reduced pressure, and n-hexane was added to the residue obtained. The resulting crystals were collected by filtration to obtain 31.3 g (yield: 55.5%) of methyl 4-carboxymethyl-2,3,5,6-tetrafluorobenzoate.

IR (KBr) cm$^{-1}$: $\nu_{C=O}$ 1735, 1720(sh)

The following compound was obtained in the same manner:
Ethyl 4-carboxymethyl-2,3,5-trifluorobenzoate
IR (KBr) cm$^{-1}$: $\nu_{C=O}$ 1710

REFERENCE EXAMPLE 2

In 50 ml of diethyl ether was dissolved 31.3 g of methyl 4-carboxymethyl-2,3,5,6-tetrafluorobenzoate. Into the resulting solution was dropped a diphenyldiazomethane-petroleum ether solution at room temperature until the color of the solution become slight reddish. The resulting crystals were collected by filtration to obtain 8.6 g (yield: 95.7%) of methyl 4-diphenylmethoxycarbonylmethyl-2,3,5,6-tetrafluorobenzoate.

IR (KBr) cm$^{-1}$: $\nu_{C=O}$ 1730

The following compound was obtained in the same manner:
Ethyl 4-diphenylmethoxycarbonylmethyl-2,3,5-trifluorobenzoate
IR (KBr) cm$^{-1}$: $\nu_{C=O}$ 1730

REFERENCE EXAMPLE 3

In 486 ml of N,N-dimethylformamide was dissolved 8.6 g of methyl 4-diphenylmethoxycarbonylmethyl-2,3,5,6tetrafluorobenzoate. To the resulting solution were added 3.54 g of paraformaldehyde and 61 mg of sodium methylate in this order. The resulting mixture was stirred at room temperature for 2 hours. To the reaction mixture were added 300 ml of ethyl acetate and 800 ml of water in this order. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=10/1) to obtain 35.0 g (yield: 67.0%) of methyl 4-(1-diphenylmethoxycarbonyl-2-hydroxyethyl)-2,3,5,6-tetrafluorobenzoate.

IR (neat) cm$^{-1}$: $\nu_{C=O}$ 1735

The following compound was obtained in the same manner:
Ethyl 4-(1-diphenylmethoxycarbonyl-2-hydroxyethyl)-2,3,5-trifluorobenzoate
IR (neat) cm$^{-1}$: $\nu_{C=O}$ 1720

REFERENCE EXAMPLE 4

In 175 ml of methylene chloride was dissolved 35.0 g of methyl 4-(1-diphenylmethoxycarbonyl-2-hydroxyethyl)-2,3,5,6-tetrafluorobenzoate. To the solution was added 7.9 g of methanesulfonyl chloride with ice-cooling. Into the mixture was dropped 16.8 g of triethylamine in 10 minutes. The resulting mixture was stirred at the same temperature for 1 hour, and 200 ml of water was added to the reaction mixture. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure to obtain 33.0 g (yield: 97.9%) of methyl 4-(1-diphenylmethoxycarbonylvinyl)-2,3,5,6-tetrafluorobenzoate.

IR (neat) cm$^{-1}$: $\nu_{C=O}$ 1730

The following compound was obtained in the same manner:

Ethyl 4-(1-diphenylmethoxycarbonylvinyl)-2,3,5-trifluorobenzoate

IR (neat) cm$^{-1}$: $\nu_{C=O}$ 1720

REFERENCE EXAMPLE 5

In 30 ml of diethyl ether was dissolved 3.08 g of ethyl 4-(1-diphenylmethoxycarbonylvinyl)-2,3,5-trifluorobenzoate. To the resulting solution was added, with ice-cooling, a diazomethane-diethyl ether solution prepared from 2.00 g of N-methyl-N-nitrosourea. The resulting mixture was stirred at room temperature for 12 hours. The reaction mixture was concentrated under reduced pressure. The residue obtained was dissolved in 30 ml of toluene. The resulting solution was stirred at 60° C. for 1 hour. The reaction mixture was concentrated under reduced pressure. The residue obtained was purified by a column chromatography (eluant: toluene) to obtain 2.90 g (yield: 91.2%) of ethyl 4-(1-diphenylmethoxycarbonyl-2-methylvinyl)-2,3,5-trifluorobenzoate.

IR (neat) cm$^{-1}$: $\nu_{C=O}$ 1715

REFERENCE EXAMPLE 6

In 15 ml of anisole was dissolved 3.2 g of methyl 4-(1-diphenylmethoxycarbonylvinyl)-2,3,5,6-tetrafluorobenzoate. To the resulting solution was added 15 ml of trifluoroacetic acid. The resulting mixture was stirred at room temperature for 1 hour. The reaction mixture was concentrated under reduced pressure. The residue obtained was mixed with 20 ml of n-hexane. The resulting mixture was adjusted to pH 7.5 with a saturated aqueous sodium hydrogencarbonate solution. The aqueous layer was separated and mixed with 50 ml of ethyl acetate. The resulting mixture was adjusted to pH 1 with 6N hydrochloric acid. The organic layer was separated, washed with water and a saturated aqueous sodium chloride solution in this order, and dried over anhydrous magnesium sulfate. The solvent was removed by distillation under reduced pressure to obtain 1.9 g (yield: 95.0%) of methyl 4-(1-carboxyvinyl)-2,3,5,6-tetrafluorobenzoate.

IR (KBr) cm$^{-1}$: $\nu_{C=O}$ 1730, 1695

The following compound was obtained in the same manner:

Ethyl 4-(1-carboxyvinyl)-2,3,5-trifluorobenzoate
IR (KBr) cm$^{-1}$: $\nu_{C=O}$ 1710, 1695(sh)

REFERENCE EXAMPLE 7

In 20 ml of N,N-dimethylformamide was dissolved 3.0 g of methyl 4-(1-carboxyvinyl)-2,3,5,6-tetrafluorobenzoate. The resulting solution was stirred at 130°–140° C. for 1.5 hours. The reaction mixture was concentrated under reduced pressure. The residue obtained was purified by a column chromatography (eluant: toluene/n-hexane=1/1) to obtain 2.0 g (yield: 79.1%) of methyl 2,3,5,6-tetrafluoro-4-vinylbenzoate.

IR (neat) cm$^{-1}$: $\nu_{C=O}$ 1740

The following compound was obtained in the same manner:

Ethyl 2,3,5-trifluoro-4-vinylbenzoate
IR (neat) cm$^{-1}$: $\nu_{C=O}$ 1720

REFERENCE EXAMPLE 8

In 10 ml of diethyl ether was dissolved 2.0 g of methyl 2,3,5,6-tetrafluoro-4-vinylbenzoate. To the resulting solution was added, with ice-cooling, a diazomethane-diethyl ether solution prepared from 3.0 g of N-methyl-N-nitrosourea. The resulting mixture was stirred at room temperature for 2 hours. The reaction mixture was concentrated under reduced pressure. The residue obtained was dissolved in 15 ml of xylene and the resulting solution was refluxed for 1 hour. The reaction mixture was concentrated under reduced pressure to obtain 2.1 g (yield: 99.1%) of methyl 4-cyclopropyl-2,3,5,6-tetrafluorobenzoate.

IR (neat) cm$^{-1}$: $\nu_{C=O}$ 1735

The following compound was obtained in the same manner:

Ethyl 4-cyclopropyl-2,3,5-trifluorobenzoate
IR (neat) cm$^{-1}$: $\nu_{C=O}$ 1715

REFERENCE EXAMPLE 9

In 330 ml of N,N-dimethylformamide was suspended 3.7 g of 60% sodium hydride. To the resulting suspension was added 20.2 g of trimethylsulfoxonium iodide with ice-cooling. The resulting mixture was stirred at room temperature for 1 hour. Thereto was added 33.0 g of methyl 4-(1-diphenylmethoxycarbonylvinyl)-2,3,5,6-tetrafluorobenzoate. The resulting mixture was stirred at the same temperature for 2 hours. To the reaction mixture were added 300 ml of ethyl acetate and 900 ml of water in this order. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene) to obtain 22.5 g (yield: 66.1%) of methyl 4-(1-diphenylmethoxycarbonylcyclopropyl)-2,3,5,6-tetrafluorobenzoate.

IR (neat) cm$^{-1}$: $\nu_{C=O}$ 1735

The following compounds were obtained in the same manner:

Ethyl 4-(1-diphenylmethoxycarbonylcyclopropyl)-2,3,5-trifluorobenzoate
IR (KBr) cm$^{-1}$: $\nu_{C=O}$ 1725

Ethyl 4-(1-diphenylmethoxycarbonyl-2-methylcyclopropyl)-2,3,5-trifluorobenzoate
IR (neat) cm$^{-1}$: $\nu_{C=O}$ 1715

REFERENCE EXAMPLE 10

In 60 ml of anisole was dissolved 22.5 g of methyl 4-(1-diphenylmethoxycarbonylcyclopropyl)-2,3,5,6tetrafluorobenzoate. To the resulting solution was added 80 ml of trifluoroacetic acid. The resulting mixture was stirred at room temperature for 2 hours. The reaction mixture was concentrated under reduced pressure. n-Hexane was added to the residue obtained. The resulting crystals were collected by filtration to obtain 12.7 g (yield: 88.8%) of methyl 4-(1-carboxycyclopropyl)-2,3,5,6tetrafluorobenzoate.

IR (KBr) cm$^{-1}$: $\nu_{C=O}$ 1745, 1690

The following compounds were obtained in the same manner:

Ethyl 4-(1-carboxycyclopropyl)-2,3,5-trifluorobenzoate

IR (KBr) cm$^{-1}$: $\nu_{C=O}$ 1715, 1685

Ethyl 4-(1-carboxy-2-methylcyclopropyl)-2,3,5-trifluorobenzoate

IR (KBr) cm$^{-1}$: $\nu_{C=O}$ 1715, 1690

REFERENCE EXAMPLE 11

500 mg of methyl 4-(1-carboxycyclopropyl)-2,3,5,6-tetrafluorobenzoate was directly heated with a burner for about 20 seconds to complete decarboxylation. The residue obtained was purified by a column chromatography (eluant: toluene) to obtain 210 mg (yield: 49.5%) of methyl 4-cyclopropyl-2,3,5,6-tetrafluorobenzoate.

The following compound was obtained in the same manner:

Ethyl 4-cyclopropyl-2,3,5-trifluorobenzoate

The physical properties of these compounds were identical with those in Reference Example 8.

REFERENCE EXAMPLE 12

In 90 ml of N,N-dimethylformamide was dissolved 9.0 g of methyl 4-(1-carboxycyclopropyl)-2,3,5,6-tetrafluorobenzoate. To the resulting solution were added, with ice-cooling, 4.0 g of ethyl chlorocarbonate and 3.7 g of triethylamine in this order. The resulting mixture was stirred at the same temperature for 30 minutes. Then, 2.6 g of sodium azide was added thereto with ice-cooling. The resulting mixture was stirred at the same temperature for 1 hour. To the reaction mixture were added 150 ml of ethyl acetate and 300 ml of water in this order. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was dissolved in a mixture of 90 ml of dioxane and 8.1 g of benzyl alcohol. The resulting solution was refluxed for 1 hour. The reaction mixture was concentrated under reduced pressure. The residue obtained was purified by a column chromatography (eluant: toluene) to obtain 10.6 g (yield: 86.9%) of methyl 4-(1-benzyloxycarbonylaminocyclopropyl)-2,3,5,6-tetrafluorobenzoate.

IR (KBr) cm$^{-1}$: $\nu_{C=O}$ 1740, 1700

The following compounds were obtained in the same manner:

Ethyl 4-(1-benzyloxycarbonylaminocyclopropyl)-2,3,5-trifluorobenzoate

IR (KBr) cm$^{-1}$: $\nu_{C=O}$ 1735, 1700

Ethyl 4-(1-benzyloxycarbonylamino-2-methylcyclopropyl)-2,3,5-trifluorobenzoate

IR (neat) cm$^{-1}$: $\nu_{C=O}$ 1710

REFERENCE EXAMPLE 13

(1) In 160 ml of methylene chloride was dissolved 15.65 g of ethyl 2,3,5-trifluoro-4-vinylbenzoate. To the resulting solution was added 11.40 g of bromine. The resulting mixture was stirred at room temperature for 3 hours, and 100 ml of water was added to the reaction mixture. The organic layer was separated, washed with water and a saturated aqueous sodium chloride solution in this order, and dried over anhydrous magnesium sulfate. The solvent was removed by distillation under reduced pressure. The residue obtained was dissolved in 100 ml of methylene chloride. To the resulting solution was added, with ice-cooling, 20.7 g of 1,8-diazabicyclo[5.4.0]undec-7-ene. The resulting mixture was stirred at room temperature for 1 hour. To the reaction mixture was added 100 ml of water. The resulting mixture was adjusted to pH 1.5 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was dissolved in 30 ml of N,N-dimethylformamide.

(2) In 150 ml of N,N-dimethylformamide was suspended 1.90 g of 60% sodium hydride. Into the resulting suspension was dropped 10.15 g of di-tert-butyl malonate in 15 minutes with ice-cooling. The resulting mixture was stirred at the same temperature for 1 hour. The N,N-dimethylformamide solution obtained in (1) above was dropped thereinto in 5 minutes with ice-cooling. The resulting mixture was stirred at room temperature for 12 hours. The reaction mixture was added to a mixture of 250 ml of ethyl acetate and 300 ml of water. The resulting mixture was adjusted to pH 3 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene) to obtain 12.69 g (yield: 42.0%) of ethyl 4-(2,2-di-tert-butoxycarbonylcyclopropyl)-2,3,5trifluorobenzoate.

IR (KBr) cm$^{-1}$: $\nu_{C=O}$ 1720(sh), 1710

REFERENCE EXAMPLE 14

18 ml of trifluoroacetic acid was added to 9.3 g of ethyl 4-(2,2-di-tert-butoxycarbonylcyclopropyl)- 2,3,5-trifluorobenzoate. The resulting mixture was stirred at room temperature for 12 hours. The reaction mixture was concentrated under reduced pressure. The residue obtained was directly heated with a burner for about 20 seconds to complete decarboxylation. To the reaction mixture were added 100 ml of diethyl ether and 200 ml of water in this order. The resulting mixture was adjusted to pH 9.5 with a 10% aqueous sodium carbonate solution. The aqueous layer was separated and 100 ml of diethyl ether was added thereto. The resulting mixture was adjusted to pH 1.5 with 2N hydrochloric acid. The organic layer was separated, washed with water and a saturated aqueous sodium chloride solution in this order, and dried over anhydrous magnesium sulfate. The solvent was removed by distillation under reduced pressure to obtain 3.30 g (yield: 54.7%) of ethyl 4-(2-carboxycyclopropyl)-2,3,5-trifluorobenzoate.

IR (KBr) cm$^{-1}$: $\nu_{C=O}$ 1725(sh), 1700

REFERENCE EXAMPLE 15

In 10 ml of tert-butyl acetate was dissolved 1.00 g of ethyl 4-(2-carboxycyclopropyl)-2,3,5-trifluorobenzoate. To the resulting solution was added 0.2 ml of a 70% aqueous perchloric acid solution. The resulting mixture was stirred at room temperature for 1 hour. To the reaction mixture were added 40 ml of ethyl acetate and 20 ml of water in this order. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: n-hexane/toluene=1/1) to obtain 0.81 g (yield: 68.1%) of ethyl 4-(2-tert-butoxycarbonylcyclopropyl)-2,3,5trifluorobenzoate.

IR (neat) cm$^{-1}$: $\nu_{C=O}$ 1720

REFERENCE EXAMPLE 16

In 60 ml of anhydrous tetrahydrofuran was dissolved 6.00 g of ethyl 4-(2-carboxycyclopropyl)-2,3,5-trifluorobenzoate. To the resulting solution was added 42 ml of a 1M solution of borane in tetrahydrofuran with ice-cooling. The resulting mixture was stirred for 1.5 hours at room temperature. The reaction mixure was added to a mixture of 100 ml of ethyl acetate and 100 ml of water. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=4/1) to obtain 4.40 g (yield: 77.1%) of ethyl 4-(2-hydroxymethylcyclopropyl)-2,3,5-trifluorobenzoate.

IR (neat) cm$^{-1}$: $\nu_{C=O}$ 1720

REFERENCE EXAMPLE 17

In 60 ml of methylene chloride was dissolved 4.00 g of ethyl 4-(2-hydroxymethylcyclopropyl)-2,3,5trifluorobenzoate. To the resulting solution were added 1.62 g of triethylamine and 1.84 g of methanesulfonyl chloride in this order with ice-cooling. The resulting mixture was stirred at room temperature for 2 hours, and 60 ml of water was added to the reaction mixture. The resulting mixture was adjusted to pH 1 with 2N hydrochloric acid. The organic layer was separated, washed with water, a saturated aqueous sodium hydrogencarbonate solution and a saturated aqueous sodium chloride solution in this order, and dried over anhydrous magnesium sulfate. The solvent was removed by distillation under reduced pressure. The residue obtained was dissolved in 60 ml of N,N-dimethylformamide. To the resulting solution was added 3.42 g of potassium salt of tert-butyl methyliminodicarboxylate with ice-cooling. The resulting mixture was stirred at room temperature for 48 hours. The reaction mixture was added to a mixture of 100 ml of ethyl acetate and 100 ml of water. The resulting mixture was adjusted to pH 1.5 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene/ ethyl acetate=20/1) to obtain 5.22 g (yield: 82.9%) of ethyl 4-[2-(N-tert-butoxycarbonyl-N-methoxycarbonylaminomethyl)cyclopropyl]-2,3,5-trifluorobenzoate.

IR (neat) cm$^{-1}$: $\nu_{C=O}$ 1780, 1740(sh), 1715

REFERENCE EXAMPLE 18

In 60 ml of ethanol was dissolved 5.22 g of ethyl 4-[2-(N-tert-butoxycarbonyl-N-methoxycarbonylaminomethyl)cyclopropyl]-2,3,5-trifluorobenzoate. To the resulting solution was added 60 ml of a 1N aqueous sodium hydroxide solution. The resulting mixture was stirred at room temperature for 2 hours. To the reaction mixture was added 60 ml of water and the resulting mixture was adjusted to pH 8 with 6N hydrochloric acid. Then, 150 ml of ethyl acetate was added thereto. The aqueous layer was separated and 100 ml of ethyl acetate was added thereto. The resulting mixture was adjusted to pH 2 with 6N hydrochloric acid. The organic layer was separated, washed with water and a saturated aqueous sodium chloride solution in this order, and dried over anhydrous magnesium sulfate. The solvent was removed by distillation under reduced pressure to obtain 4.10 g (98.1%) of 4-(2-tert-butoxycarbonylaminomethylcyclopropyl)-2,3,5-trifluorobenzoic acid.

IR (KBr) cm$^{-1}$: $\nu_{C=O}$ 1720, 1700

REFERENCE EXAMPLE 19

In a mixture of 14 ml of methanol and 14 ml of dioxane was dissolved 1.8 g of methyl 4-(1-benzyloxycarbonylaminocyclopropyl)-2,3,5,6-tetrafluorobenzoate.
To the resulting solution was added 14 ml of a 1N aqueous sodium hydroxide solution. The resulting mixture was stirred at room temperature for 1 hour. To the reaction mixture was added 50 ml of water. The resulting mixture was adjusted to pH 1 with 2N hydrochloric acid, and 50 ml of ethyl acetate was added thereto. The organic layer was separated, washed with water and a saturated aqueous sodium chloride solution in this order, and dried over anhydrous magnesium sulfate. The solvent was removed by distillation under reduced pressure, and n-hexane was added to the residue obtained. The resulting crystals were collected by filtration to obtain 1.7 g (yield: 97.7%) of 4-(1-benzyloxycarbonylaminocyclopropyl)-2,3,5,6tetrafluorobenzoic acid.

IR (KBr) cm$^{-1}$: $\nu_{C=0}$ 1735

The compounds shown in Table 2 were obtained in the same manner. $R^2$ and

in Table 2 correspond to those in the following formula:

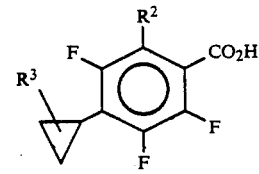

TABLE 2

| $-R^2$ | $R^3$ | IR (KBr) cm$^{-1}$: $\nu_{C=0}$ |
|---|---|---|
| $-H$ | (cyclopropyl) | 1700 |
| $-H$ | NHZ (cyclopropyl) | 1710, 1675 |

TABLE 2-continued

| —R² | R³ (cyclopropyl) | IR (KBr) cm⁻¹: $\nu_{C=O}$ |
|---|---|---|
| —H | ◁-COO-+ | 1710 |
| —H | ◁(NHZ)(Me) | 1715, 1665 |
| —F | ◁ | 1705 |

REFERENCE EXAMPLE 20

(1)(i) To 1.50 g of 4-(1-benzyloxycarbonylaminocyclopropyl)-2,3,5,6-tetrafluorobenzoic acid were added 4.66 g of thionyl chloride and 0.1 ml of N,N-dimethylformamide in this order. The resulting mixture was stirred at 40°–50° C. for 1 hour. The reaction mixture was concentrated under reduced pressure. The residue obtained was dissolved in 20 ml of toluene.

(1)(ii) In 10 ml of anhydrous tetrahydrofuran was suspended 470 mg of 60% sodium hydride. Into the resulting suspension was dropped 2.20 g of tert-butyl ethyl malonate in 15 minutes with ice-cooling. The resulting mixture was stirred at the same temperature for 20 minutes. The reaction mixture was cooled to −20° C., and the toluene solution obtained in (1)(i) above was dropped thereinto in 10 minutes at the same temperature. The resulting mixture was stirred at −20° C. to −10° C. for 30 minutes. To the reaction mixture were added 20 ml of ethyl acetate and 20 ml of water in this order. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. To the residue obtained was added 10 ml of trifluoroacetic acid. The resulting mixture was stirred at room temperature for 12 hours. The reaction mixture was concentrated under reduced pressure. To the residue obtained were added 20 ml of ethyl acetate and 20 ml of water in this order. The organic layer was separated, washed with a saturated aqueous sodium hydrogencarbonate solution, water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=20/1) to obtain 1.56 g (yield: 87.6%) of ethyl 4-(1-benzyloxycarbonylaminocyclopropyl)-2,3,5,6-tetrafluorobenzoylacetate.

IR (KBr) cm⁻¹: $\nu_{C=O}$ b 1710

The following compound was obtained in the same manner:

Ethyl 4-cyclopropyl-2,3,5,6-tetrafluorobenzoylacetate

IR (neat) cm⁻¹: $\nu_{C=O}$ 1745, 1705

(2) In 75 ml of anhydrous tetrahydrofuran was dissolved 7.50 g of 4-(1-benzyloxycarbonylaminocyclopropyl)-2,3,5-trifluorobenzoic acid. To the resulting solution was added 4.99 g of N,N'-carbonyldiimidazole with ice-cooling. The resulting mixture was stirred at room temperature for 1 hour. Thereto was added 4.40 g of magnesium ethoxycarbonylacetate. The resulting mixture was stirred at the same temperature for 20 hours. The reaction mixture was added to a mixture of 150 ml of ethyl acetate and 200 ml of water. The resulting mixture was adjusted to pH 1 with 2N hydrochloric acid. The organic layer was separated, washed with a saturated aqueous sodium hydrogencarbonate solution, water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=50/1) to obtain 8.10 g (yield: 90.6%) of ethyl 4-(1-benzyloxycarbonylaminocyclopropyl)-2,3,5-trifluorobenzoylacetate.

IR (neat) cm⁻¹: $\nu_{C=O}$ 1725, 1700(sh)

The compounds shown in Table 3 were obtained in the same manner.

in Table 3 corresponds to that in the following formula:

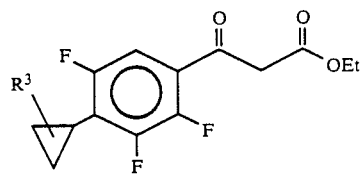

TABLE 3

| R³ (cyclopropyl) | IR cm⁻¹: $\nu_{C=O}$ |
|---|---|
| ◁ | (neat) 1740, 1685 |
| ◁-COO-+ | (neat) 1720, 1700(sh) |
| ◁(NHZ)(Me) | (neat) 1730, 1700(sh) |
| ◁-NHBoc | (KBr) 1740(sh), 1670 |

REFERENCE EXAMPLE 21

(1) In 30 ml of benzene was dissolved 3.00 g of ethyl 4-(1-benzyloxycarbonylaminocyclopropyl)- 2,3,5-trifluorobenzoylacetate. To the resulting solution was added 3.69 g of N,N-dimethylformamide-dimethylacetal. The resulting mixture was refluxed for 30 minutes. The reaction mixture was concentrated under reduced pressure. The residue obtained was dissolved in 15 ml of toluene. To the resulting solution was added 518 mg of DL-2-amino-1-propanol. The resulting mixture was stirred at room temperature for 17 hours. The reaction mixture was concentrated under reduced pressure. The residue obtained was purified by a column chromatography (eluant: toluene/ethyl acetate=5/1) to obtain 3.09 g (yield: 86.1%) of ethyl 2-[4-(1-benzyloxycarbonylaminocyclopropyl)-2,3,5trifluorobenzoyl]-3-(2-hydroxy-1-methylethylamino)acrylate.

IR (KBr) cm$^{-1}$: $\nu_{C=O}$ 1690

The compounds shown in Table 4 were obtained in the same manner.

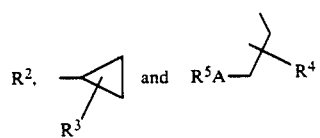

in Table 4 correpond to those in the following formula:

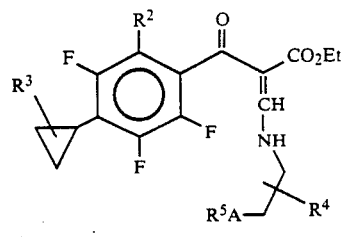

TABLE 4

| —R² | R³ / (cyclopropyl) | R⁵A—R⁴ | IR cm$^{-1}$: $\nu_{C=O}$ |
|---|---|---|---|
| —H | (cyclopropyl) | HO–CH₂–CH(Me)– | (neat) 1665 |
| —H | NHZ-cyclopropyl | HO–CH₂–C*(H)(Me) | (KBr) 1695 |
| —H | cyclopropyl-COO-t-Bu | HO–CH₂–C*(H)(Me) | (neat) 1715 |
| —H | NHZ-cyclopropyl-Me | HO–CH₂–C*(H)(Me) | (KBr) 1690 |
| —H | cyclopropyl-CH₂-NHBoc | HO–CH₂–C*(H)(Me) | (KBr) 1680 |
| —H | NHZ-cyclopropyl | HO–CH₂–C*(H)(Et) | (KBr) 1690 |
| —H | NHZ-cyclopropyl | HO–CH₂–CH(CH₂OTHP)– | (neat) 1690 |
| —H | NHZ-cyclopropyl | HO–CH₂–CH(CH₂F)– | (KBr) 1690 |
| —H | NHZ-cyclopropyl | HO–CH₂–C(Me)(Me)– | (KBr) 1690 |
| —H | NHZ-cyclopropyl | HO–CH₂–cyclopropyl | (KBr) 1700 |
| —H | NHZ-cyclopropyl | HO–CH₂–CH₂–CH₃ | (KBr) 1690 |

TABLE 4-continued

| —R² | R³ | R⁵A—R⁴ | IR cm⁻¹: $\nu_{C=O}$ |
|---|---|---|---|
| —H | NHZ 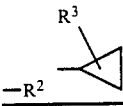 | 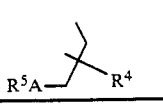 MeN(Boc)–CH₂–CH(Me)(H) | (KBr) 1690 |
| —F | 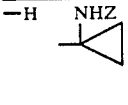 | 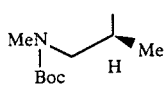 HO–CH₂–CH(Me) | (KBr) 1695 |
| —F | NHZ 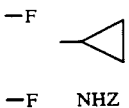 | 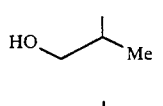 HO–CH₂–CH(Me) | (KBr) 1685 |

(2) In 5 ml of benzene was dissolved 500 mg of ethyl 4-(1-benzyloxycarbonylaminocyclopropyl)-2,3,5-trifluorobenzoylacetate. To the resulting solution was added 411 mg of N,N-dimethylformamide-dimethylacetal, and the resulting mixture was refluxed for 40 minutes. The reaction mixture was concentrated under reduced pressure, and the residue obtained was dissolved in 5 ml of ethanol. To the resulting solution were added 157 mg of 2-aminothioethanol hydrochloride and 139 mg of triethylamine, and the resulting mixture was stirred at room temperature for 16 hours. The reaction mixture was concentrated under reduced pressure and the residue obtained was purified by a column chromatography (eluant: toluene/ethyl acetate=5/1) to obtain 250 mg (yield: 41.7%) of ethyl 2-[4-(1-benzyloxycarbonylaminocyclopropyl)-2,3,5-trifluorobenzoyl]-3-(2-mercaptoethylamino)acrylate.

IR (KBr) cm⁻¹: $\nu_{C=O}$ 1695

REFERENCE EXAMPLE 22

In 3 ml of N,N-dimethylformamide was dissolved 300 mg of ethyl 2-(4-cyclopropyl-2,3,5,6-tetrafluorobenzoyl)-3-(2-hydroxy-1-methylethylamino)acrylate. To the resulting solution was added 130 mg of potassium carbonate. The resulting mixture was stirred at 80°–90° C. for 30 minutes, and 20 ml of water was added to the reaction mixture. The resulting crystals were collected by filtration to obtain 240 mg (yield: 84.5%) of ethyl 7-cyclopropyl-5,6,8-trifluoro-1-(2-hydroxy-1-methylethyl)-1,4-dihydro-4-oxo-3-quinolinecarboxylate.

IR (KBr) cm⁻¹: $\nu_{C=O}$ 1725, 1705

The following compound was obtained in the same manner:

Ethyl (S)-7-(1-benzyloxycarbonylaminocyclopropyl)-6,8-difluoro-1-[2-(N-tert-butoxycarbonyl-N-methylamino)-1-methylethyl]-1,4-dihydro-4-oxo-3-quinolinecarboxylate IR (KBr) cm⁻¹: $\nu_{C=O}$ 1720, 1680

REFERENCE EXAMPLE 23

To 2 ml of trifluoroacetic acid was added, with ice-cooling, 300 mg of ethyl (S)-7-(1-benzyloxycarbonylaminocyclopropyl)-6,8-difluoro-1-[2-(N-tert-butoxycarbonyl-N-methylamino)-1-methylethyl]-1,4-dihydro-4-oxo-3-quinolinecarboxylate. The resulting mixture was stirred at the same temperature for 2.5 hours. The reaction mixture was concentrated under reduced pressure. To the residue obtained were added 20 ml of ethyl acetate and 10 ml of water in this order. The resulting mixture was adjusted to pH 8 with a saturated aqueous sodium hydrogencarbonate solution. The organic layer was separated, washed with water and a saturated aqueous sodium chloride solution in this order, and dried over anhydrous magnesium sulfate. The solvent was removed by distillation under reduced pressure to obtain 240 mg (yield: 96.0%) of ethyl (S)-7-(1-benzyloxycarbonylaminocyclopropyl)-6,8-difluoro-1-[2-(N-methylamino)-1methylethyl]-1,4-dihydro-4-oxo-3-quinolinecarboxylate.

IR (KBr) cm⁻¹: $\nu_{C=O}$ 1720, 1685

EXAMPLE 1

In 1.7 ml of N,N-dimethylformamide was dissolved 170 mg of ethyl 7-cyclopropyl-5,6,8-trifluoro-1-(2-hydroxy-1-methylethyl)-1,4-dihydro-4-oxo-3-quinolinecarboxylate. To the resulting solution was added 20 mg of 60% sodium hydride. The resulting mixture was stirred at 80°–90° C. for 15 hours. The reaction mixture was added to a mixture of 5 ml of ethyl acetate and 5 ml of water. The resulting mixture was adjusted to pH 1.5 with 2N hydrochloric acid. The resulting crystals were collected by filtration to obtain 63 mg (yield: 39.1%) of ethyl 10-cyclopropyl-8,9-difluoro-3-methyl-7-oxo-2,3-dihydro-7H-pyrido[1,2,3-de][1,4]benzoxazine-6-carboxylate.

IR (KBr) cm⁻¹: $\nu_{C=O}$ 1725, 1690

EXAMPLE 2

In 5 ml of N,N-dimethylformamide was dissolved 240 mg of ethyl (S)-7-(1-benzyloxycarbonylaminocyclopropyl)-6,8-difluoro-1-[2-(N-methylamino)-1-methylethyl]-1,4-dihydro-4-oxo-3-quinolinecarboxylate. To the resulting solution was added 80 mg of potassium carbonate. The resulting mixture was stirred at room temperature for 6 hours. The reaction mixture was added to a mixture of 20 ml of ethyl acetate and 20 ml of water. The resulting mixture was adjusted to pH 3 with 2N hydrochloric acid. The organic layer was separated, washed with water and a saturated aqueous sodium chloride solution in this order, and dried over anhydrous magnesium sulfate. The solvent was removed by distillation under reduced pressure. Diethyl ether was added to the residue obtained. The resulting crystals were collected by filtration to obtain 120 mg (yield: 52.2%) of ethyl (S)-10-(1-benzyloxycarbonylaminocyclopropyl)-9-fluoro-1,3-dimethyl-7-oxo-2,3-dihydro-1H,7H-pyrido[1,2,3-de]-quinoxaline-6-carboxylate.

IR (KBr) cm⁻¹: $\nu_{C=O}$ 1715

EXAMPLE 3

In 25 ml of N,N-dimethylformamide was dissolved 3.07 g of ethyl 2-[4-(1-benzyloxycarbonylaminocyclopropyl)-2,3,5-trifluorobenzoyl]-3-(2-hydroxy-1-methylethylamino)acrylate. To the resulting solution was added 519 mg of 60% sodium hydride with ice-cooling. The resulting mixture was stirred at room temperature for 18 hours. The reaction mixture was added to a mixture of 50 ml of ethyl acetate and 50 ml of water. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=1/1) to obtain 760 mg (yield: 26.9%) of ethyl 10-(1-benzyloxycarbonylaminocyclopropyl)-9-fluoro-3-methyl-7-oxo-2,3-dihydro-7H-pyrido[1,2,3-de][1,4]benzoxazine-6-carboxylate.

IR (KBr) cm$^{-1}$: $\nu_{C=O}$ 1715

The compounds shown in Table 5 were obtained in the same manner. $R^2$ in Table 5 corresponds to that in the following formula:

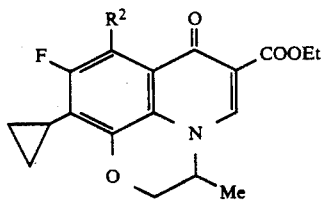

TABLE 5

| $-R^2$ | IR (KBr) cm$^{-1}$: $\nu_{C=O}$ |
|---|---|
| —H | 1715, 1685 |
| —F | 1725, 1690 |

EXAMPLE 4

In 20 ml of N,N-dimethylformamide was dissolved 2.07 g of ethyl 2-[4-(1-benzyloxycarbonylaminocyclopropyl)-2,3,5,6-tetrafluorobenzoyl]-3-(2-hydroxy-1methylethylamino)acrylate. To the resulting solution was added 1.17 g of potassium carbonate. The resulting mixture was stirred at 90°-100° C. for 3.5 hours. The reaction mixture was added to a mixture of 40 ml of ethyl acetate and 40 ml of water. The resulting mixture was adjusted to pH 1.5 with 2N hydrochloric acid. The organic layer was separated, washed with water and a saturated aqueous sodium chloride solution in this order, and dried over anhydrous magnesium sulfate. The solvent was removed by distillation under reduced pressure. Diethyl ether was added to the residue obtained. The resulting crystals were collected by filtration to obtain 1.40 g (yield: 72.9%) of ethyl 10-(1-benzyloxycarbonylaminocyclopropyl)-8,9-difluoro-3-methyl-7-oxo-2,3-dihydro-7H-pyrido benzoxazine-6-carboxylate.

IR (KBr) cm$^{-1}$: $\nu_{C=O}$ 1720

The compounds shown in Table 6 were obtained in the same manner.

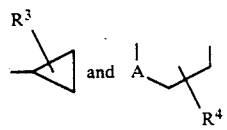

in Table 6 correspond to those in the following formula:

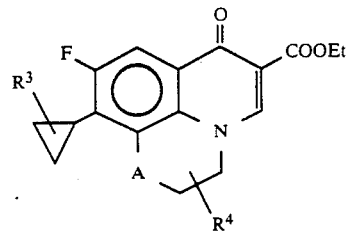

TABLE 6

| $R^3$ | A, $R^4$ | IR (KBr) cm$^{-1}$: $\nu_{C=O}$ |
|---|---|---|
| NHZ (cyclopropyl) | O, Me, H | 1715 |
| cyclopropyl-COO+ | O, Me, H | 1720 |
| NHZ (cyclopropyl-Me) | O, Me, H | 1720 |
| cyclopropyl-CH₂-NHBoc | O, Me, H | 1715 |
| NHZ (cyclopropyl) | O, Et, H | 1715 |
| NHZ (cyclopropyl) | O, OTHP | 1720 |
| NHZ (cyclopropyl) | O, CH₂F | 1715, 1680 |
| NHZ (cyclopropyl) | O, Me, Me | 1720 |
| NHZ (cyclopropyl) | O, cyclopropyl | 1725, 1695 |
| NHZ (cyclopropyl) | O, (propyl) | 1710 |

TABLE 6-continued

| R³ ⟨△⟩ | A R⁴ | IR (KBr) cm⁻¹: $\nu_{C=0}$ |
|---|---|---|
| NHZ ⟨△⟩ | S | 1715 |

EXAMPLE 5

In 2 ml of ethanol was dissolved 90 mg of ethyl 10-(1-benzyloxycarbonylaminocyclopropyl)-9-fluoro-3-(2-tetrahydropyranyloxymethyl)-7-oxo-2,3-dihydro-7H-pyrido[1,2,3-de][1,4]benzoxazine-6-carboxylate. To the resulting solution was added 10 mg of p-toluenesulfonic acid monohydrate. The resulting mixture was stirred at room temperature for 4 hours. The reaction mixture was concentrated under reduced pressure. Ethanol was added to the residue obtained, and the resulting crystals were collected by filtration to obtain 47 mg (yield: 61.0%) of ethyl 10-(1-benzyloxycarbonylaminocyclopropyl)-9-fluoro-3-hydroxymethyl-7-oxo-2,3-dihydro-7H-pyrido[1,2,3-de][1,4]-benzoxazine-6-carboxylate.

IR (KBr) cm⁻¹: $\nu_{C=0}$ 1715

EXAMPLE 6

In 4 ml of methylene chloride was suspended 380 mg of ethyl 10-(1-benzyloxycarbonylaminocyclopropyl)-9-fluoro-3-hydroxymethyl-7-oxo-2,3-dihydro-7H-pyrido[1,2,3de][1,4]benzoxazine-6-carboxylate. To the resulting suspension were added, with ice-cooling, 230 mg of triethylamine and 260 mg of methanesulfonyl chloride in this order. The resulting mixture was stirred at room temperature for 30 minutes. To the reaction mixture were added 10 ml of methylene chloride and 10 ml of water in this order. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. To the residue obtained were added 4.4 ml of benzene and 175 mg of 1,8-diazabicyclo-[5,4,0]undec-7-ene in this order. The resulting mixture was refluxed for 1 hour. The reaction mixture was added to a mixture of 20 ml of ethyl acetate and 20 ml of water. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: toluene/ethyl acetate=3/2) to obtain 260 mg (yield: 71.0%) of ethyl 10-(1-benzyloxycarbonylaminocyclopropyl)-9-fluoro-3-methylene-7-oxo-2,3-dihydro-7H-pyrido[1,2,3-de][1,4]-benzoxazine-6-carboxylate.

IR (KBr) cm⁻¹: $\nu_{C=0}$ 1720, 1685

EXAMPLE 7

5 ml of trifluoroacetic acid was added to 570 mg of ethyl (S)-10-(2-tert-butoxycarbonylcyclopropyl)-9-fluoro-3-methyl-7-oxo-2,3-dihydro-7H-pyrido[1,2,3-de][1,4]benzoxazine-6-carboxylate. The resulting mixture was stirred at room temperature for 1 hour. The reaction mixture was concentrated under reduced pressure. Diethyl ether was added to the residue obtained. The resulting crystals were collected by filtration to obtain 460 mg (yield: 92.9%) of ethyl (S)-10-(2-carboxycyclopropyl)-9-fluoro-3-methyl-7-oxo-2,3-dihydro-7H-pyrido[1,2,3-de][1,4]benzoxazine-6-carboxylate.

IR (KBr) cm⁻¹: $\nu_{C=0}$ 1720

EXAMPLE 8

In 4 ml of N,N-dimethylformamide was suspended 200 mg of ethyl (S)-10-(2-carboxycyclopropyl)-9-fluoro-3-methyl-7-oxo-2,3-dihydro-7H-pyrido[1,2,3-de][1,4]-benzoxazine-6-carboxylate. To the resulting suspension were added, with ice-cooling, 70 mg of ethyl chlorocarbonate and 65 mg of triethylamine. The resulting mixture was stirred at the same temperature for 15 minutes. To the reaction mixture was added 45 mg of sodium azide with ice-cooling. The resulting mixture was stirred at the same temperature for 1 hour. To the reaction mixture were added 20 ml of chloroform and 20 ml of water in this order. The resulting mixture was adjusted to pH 1 with 2N hydrochloric acid. The organic layer was separated, washed with water and a saturated aqueous sodium chloride solution, and dried over anhydrous magnesium sulfate. The solvent was removed by distillation under reduced pressure. To the residue obtained were added 5 ml of dioxane and 115 mg of benzyl alcohol in this order. The resulting mixture was stirred at 100° C. for 1.5 hours. The reaction mixture was concentrated under reduced pressure. The residue obtained was purified by a column chromatography (eluant: chloroform/ethanol=15/1) to obtain 160 mg (yield: 64.0%) of ethyl (S)-10-(2-benzyloxycarbonylaminocyclopropyl)-9-fluoro-3-methyl-7-oxo-2,3-dihydro-7H-pyrido[1,2,3-de][1,4]benzoxazine-6carboxylate.

IR (KBr) cm⁻¹: $\nu_{C=0}$ 1715

EXAMPLE 9

1 ml of a 30% hydrogen bromide-acetic acid solution was added to 52 mg of ethyl 10-(1-benzyloxycarbonylaminocyclopropyl)-9-fluoro-3-fluoromethyl-7-oxo-2,3-dihydro-7H-pyrido[1,2,3-de][1,4]benzoxazine-6carboxylate. The resulting mixture was stirred at room temperature for 1 hour. The reaction mixture was concentrated under reduced pressure. To the residue obtained were added 10 ml of diethyl ether and 20 ml of water in this order. The aqueous layer was separated and 20 ml of ethyl acetate was added thereto. The resulting mixture was adjusted to pH 8.5 with a saturated aqueous sodium hydrogencarbonate solution. The organic layer was separated, washed with a saturated aqueous sodium chloride solution, and dried over anhydrous magnesium sulfate. The solvent was removed by distillation under reduced pressure to obtain 35 mg (yield: 90.8%) of ethyl 10-(1-aminocyclopropyl)-9-fluoro-3-fluoromethyl-7-oxo-2,3-dihydro-7H-pyrido[1,2,3-de][1,4]benzoxazine-6-carboxylate.

IR (KBr) cm⁻¹: $\nu_{C=0}$ 1705

EXAMPLE 10

In 100 ml of acetic acid was dissolved 10 g of ethyl (S)-10-(1-benzyloxycarbonylaminocyclopropyl)-9-fluoro-3-methyl-7-oxo-2,3-dihydro-7H-pyrido[1,2,3-de][1,4]benzoxazine-6-carboxylate. To the resulting solution was added 2 g of 5% palladium-carbon. The resulting mixture was stirred at room temperature for 2 hours at atmospheric pressure in a hydrogen stream.

The reaction mixture was filtered. The filtrate was concentrated to dryness under reduced pressure. To the residue obtained were added 200 ml of methylene chloride and 200 ml of water in this order. The resulting mixture was adjusted to pH 7.7 with a saturated aqueous sodium hydrogen-carbonate solution. The organic layer was separated, washed with water and a saturated aqueous sodium chloride solution in this order, and dried over anhydrous magnesium sulfate. The solvent was removed by distillation under reduced pressure. Diethyl ether was added to the residue obtained. The resulting crystals were collected by filtration to obtain 6.43 g (yield: 89.2%) of ethyl (S)-10-(1-aminocyclopropyl)-9-fluoro-3-methyl-7-oxo-2,3-dihydro-7H-pyrido[1,2,3-de][1,4]benzoxazine-6-carboxylate.

IR (KBr) cm$^{-1}$: $\nu_{C=O}$ 1705

EXAMPLE 11

In a mixture of 2 ml of acetonitrile and 4 ml of methanol was suspended 200 mg of ethyl (S)-10-(1-aminocyclopropyl)-9-fluoro-3-methyl-7-oxo-2,3-dihydro-7H-pyrido[1,2,3-de][1,4]benzoxazine-6-carboxylate. To the resulting suspension were added 230 mg of 37% aqueous formaldehyde solution and 73 mg of sodium cyanoborohydride in this order. The resulting mixture was stirred at room temperature for 2 hours. To the reaction mixture was added 0.1 ml of acetic acid. The resulting mixture was concentrated under reduced pressure. To the residue obtained were added 20 ml of chloroform and 20 ml of water in this order. The resulting mixture was adjusted to pH 1 with 2N hydrochloric acid. The aqueous layer was separated, and 20 ml of chloroform was added thereto. The resulting mixture was adjusted to pH 7.5 with a saturated aqueous sodium hydrogen-carbonate solution. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: chloroform/ethanol=20/1) to obtain 100 mg (yield: 47.6%) of ethyl (S)-10-[1-(N,N-dimethylamino)-cyclopropyl]-9-fluoro-3-methyl-7-oxo-2,3-dihydro-7H-pyrido[1,2,3-de][1,4]benzoxazine-6-carboxylate.

IR (KBr) cm$^{-1}$: $\nu_{C=O}$ 1715

EXAMPLE 12

In 33 ml of methylene chloride was suspended 6.43 g of ethyl (S)-10-(1-aminocyclopropyl)-9-fluoro-3-methyl-7-oxo-2,3-dihydro-7H-pyrido[1,2,3-de][1,4]benzoxazine- 6-carboxylate. To the resulting suspension was added 2.27 g of acetic anhydride with ice-cooling. The resulting mixture was stirred at room temperature for 1 hour, and 30 ml of water was added to the reaction mixture. The resulting crystals were collected by filtration to obtain 5.85 g (yield: 81.1%) of ethyl (S)-10-(1-acetylaminocyclopropyl)-9-fluoro-3-methyl-7-oxo-2,3-dihydro-7H-pyrido[1,2,3-de][1,4]benzoxazine-6-carboxylate.

IR (KBr) cm$^{-1}$: $\nu_{C=O}$ 1710, 1665

EXAMPLE pb 13

In a mixture of 3 ml of anhydrous tetrahydrofuran and 1 ml of anhydrous hexamethylphosphoric triamide was dissolved 300 mg of ethyl (S)-10-(1-acetylaminocyclopropyl)-9-fluoro-3-methyl-7-oxo-2,3-dihydro-7H-pyrido[1,2,3-de][1,4]benzoxazine-6-carboxylate. To the resulting solution was added 30 mg of 60% sodium hydride with ice-cooling. The resulting mixture was stirred at the same temperature for 30 minutes. Thereto was added 340 mg of methyl iodide with ice-cooling. The resulting mixture was stirred at room temperature for 1 hour. To the reaction mixture were added 20 ml of chloroform and 20 ml of water in this order. The resulting mixture was adjusted to pH 2 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: chloroform/ethanol=15/1) to obtain 100 mg (yield: 19.2%) of ethyl (S)-10-[1-(N-acetyl-N-methylamino)cyclopropyl]-9-fluoro-3-methyl-7-oxo-2,3-dihydro 7H-pyrido[1,2,3-de][1,4]benzoxazine-6-carboxylate.

IR (KBr) cm$^{-1}$: 1715, 1645

EXAMPLE 14

To 250 mg of ethyl 10-cyclopropyl-9-fluoro-3-methyl-7-oxo-2,3-dihydro-7H-pyrido[1,2,3-de][1,4]-benzoxazine-6-carboxylate were added 2.5 ml of a 1N aqueous sodium hydroxide solution, 2.5 ml of ethanol and 2.5 ml of dioxane in this order. The resulting mixture was stirred at room temperature for 1.5 hours. To the reaction mixture were added 10 ml of water and 20 ml of ethyl acetate in this order. The resulting mixture was adjusted to pH 3 with 2N hydrochloric acid. The organic layer was separated, washed with water and a saturated aqueous sodium chloride solution, and dried over anhydrous magnesium sulfate. The solvent was removed by distillation under reduced pressure. Diethyl ether was added to the residue obtained and the resulting crystals were collected by filtration to obtain 200 mg (yield: 87.3%) of 10-cyclopropyl-9-fluoro-3-methyl-7-oxo-2,3-dihydro-7H-pyrido[1,2,3-de][1,4]benzoxazine-6-carboxylic acid.

Melting point: 263°–265° C. (recrystallized from chloroform-methanol)

IR (KBr) cm$^{-1}$: $\nu_{C=O}$ 1710

NMR (d$_1$-TFA) value:

0.90–2.00 (7H, m), 2.10–2.70 (1H, m), 4.30–5.35 (3H, m), 7.91 (1H, d, J=10.5 Hz), 9.26 (1H, s)

The compounds shown in Table 7 were obtained in the same manner.

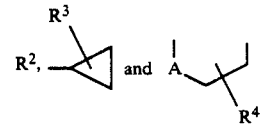

in Table 7 correspond to those in the following formula:

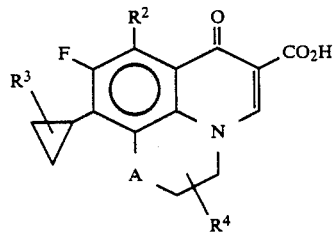

TABLE 7

| R² | R³ | A-CR⁴ group | IR (KBr) cm⁻¹: $\nu_{C=O}$ |
|---|---|---|---|
| —F | (cyclopropyl) | —O—CH(Me)— | 1725 |
| —F | NHZ-cyclopropyl | —O—CH₂—CH(Me)— | 1720 |
| —H | NHZ-cyclopropyl | —O—CH(Me)— | 1705 |
| —H | NHZ-cyclopropyl | —O—CH₂—C*H(Me)— | 1705 |
| —H | cyclopropyl-NHZ | —O—CH₂—C*H(Me)— | 1720 |
| —H | NHZ-cyclopropyl(Me) | —O—CH₂—C*H(Me)— | 1705 |
| —H | NHZ-cyclopropyl | —O—CH₂—C*H(Et)— | 1705 |
| —H | NHZ-cyclopropyl | —O—CH₂—CH(CH₂OH)— | 1715 |
| —H | NHZ-cyclopropyl | —O—CH₂—CH=CH₂ | 1720 |
| —H | NHZ-cyclopropyl | —O—CH₂—C(Me)₂— | 1720 |
| —H | NHZ-cyclopropyl | —O—CH₂—cyclopropyl | 1705 |
| —H | NHZ-cyclopropyl | —O—CH₂—cyclobutyl | 1705 |
| —H | NHZ-cyclopropyl | —S—CH₂—CH₂— | 1710 |
| —H | NHZ-cyclopropyl | MeN(H)—CH₂—C*H(Me)— | 1710 |

EXAMPLE 15

In 2 ml of N,N-dimethylformamide was dissolved 200 mg of 10-(1-benzyloxycarbonylaminocyclopropyl)-8,9-difluoro-3-methyl-7-oxo-2,3-dihydro-7H-pyrido[1,2,3-de][1,4]benzoxazine-6-carboxylic acid. To the resulting solution was added 319 mg of benzylamine. The resulting mixture was stirred at 90°–100° C. for 4.5 hours. The reaction mixture was added to a mixture of 5 ml of ethyl acetate and 5 ml of water. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. Diethyl ether was added to the residue obtained and the resulting crystals were collected by filtration to obtain 110 mg (yield: 46.4%) of 8-benzylamino-10-(1-benzyloxycarbonylaminocyclopropyl)-9-fluoro-3-methyl-7-oxo-2,3-dihydro-7H-pyrido[1,2,3-de][1,4]benzoxazine-6-carboxylic acid.

IR (KBr) cm⁻¹: $\nu_{C=O}$ 1710

The following compound was obtained in the same manner:

8-Benzylamino-10-cyclopropyl-9-fluoro-3-methyl-7-oxo-2,3-dihydro-7H-pyrido[1,2,3-de][1,4]-benzoxazine-6-carboxylic acid IR (KBr) cm⁻¹: $\nu_{C=O}$ 1695

EXAMPLE 16

In 2 ml of N,N-dimethylformamide was dissolved 230 mg of benzyl alcohol. To the resulting solution was added 85 mg of 60% sodium hydride with ice-cooling. The resulting mixture was stirred at room temperature for 30 minutes. Thereto was added, with ice-cooling, 250 mg of 10-(1-benzyloxycarbonylaminocyclopropyl)-8,9-difluoro-3-methyl-7-oxo-2,3-dihydro-7H-pyrido[1,2,3-de][1,4]-benzoxazine-6-carboxylic acid. The resulting mixture was stirred at room temperature for 7 hours. The reaction mixture was added to a mixture of 15 ml of ethyl acetate and 15 ml of water. The resulting mixture was adjusted to pH 1 with 2N hydrochloric acid. The organic layer was separated, washed with water and a saturated aqueous sodium chloride solution in this order, and dried over anhydrous magnesium sulfate. The solvent was removed by distillation under reduced pressure. The residue obtained was purified by a column chromatography (eluant: chloroform/ethanol=10/1) to obtain 73.0 mg (yield: 24.6%) of 8-benzyloxy-10-(1-benzyloxycarbonylaminocyclopropyl)-9-fluoro-3-methyl-7-oxo-2,3-dihydro-7H-pyrido[1,2,3-de][1,4]benzoxazine-6-carboxylic acid.

IR (KBr) cm⁻¹: $\nu_{C=O}$ 1715

The following compound was obtained in the same manner:

8-Benzyloxy-10-cyclopropyl-9-fluoro-3-methyl-7-oxo-2,3-dihydro-7H-pyrido[1,2,3-de][1,4]-benzoxazine-6-carboxylic acid IR (KBr) cm⁻¹: $\nu_{C=O}$ 1720

EXAMPLE 17

In 9 ml of acetic acid was dissolved 90.0 mg of 8-benzylamino-10-(1-benzyloxycarbonylaminocyclopropyl)-9-fluoro-3-methyl-7-oxo-2,3-dihydro-7H-pyrido[1,2,3-de][1,4]benzoxazine-6-carboxylic acid. To the resulting solution was added 80.0 mg of 5% palladium-carbon. The resulting mixture was stirred at room temperature for 2 hours at atmospheric pressure in a hydrogen stream. The reaction mixture was filtered. To the filtrate was added 5 ml of 2N hydrochloric acid. The resulting mixture was concentrated under reduced pressure. Ethanol was added to the residue obtained, and the resulting crystals were collected by filtration to obtain 45.9 mg (yield: 76.9%) of 8-amino-10-(1-aminocyclopropyl)-9-fluoro-3-methyl-7-oxo-2,3-dihydro-7H-pyrido[1,2,3-de][1,4]benzoxazine-6-carboxylic acid hydrochloride.

Melting point: 277°–281° C. (recrystallized from ethanol-methanol)

IR (KBr) cm$^{-1}$: $\nu_{C=O}$ 1695.

NMR (d$_1$-TFA) δ value: 1.30–2.20 (7H, m), 4.40–5.40 (3H, m), 9.25 (1H, s)

The compounds shown in Table 8 were obtained in the same manner.

in Table 8 correspond to those in the following formula:

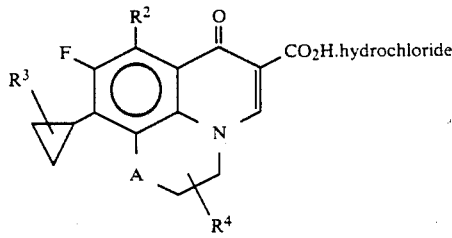

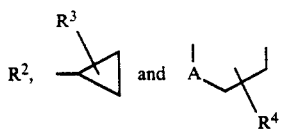

TABLE 8

| R$^2$ | R$^3$ (cyclopropyl) | A / R$^4$ group | Melting point (°C.) (solvent used for recrystallization) | IR (KBr) cm$^{-1}$: $\nu_{C=O}$ | NMR (solvent) δ value: |
|---|---|---|---|---|---|
| —F | NHZ | –O–CH$_2$–CH(Me)– | >280 (ethanol-methanol) | 1710 | (d$_1$-TFA) 1.20–2.20 (7H, m), 4.50–5.50 (3H, m), 9.35 (1H, s) |
| —OH | NH$_2$ | –O–CH$_2$–CH(Me)– | 257–261 (ethanol-methanol) | 1740 | (d$_1$-TFA) 1.20–2.20 (7H, m), 4.20–5.50 (3H, m), 9.02 (1H, s) |
| —H | NH$_2$ | –O–CH$_2$–CH(Me)– | 254–257 (methanol) | 1715 | (d$_1$-TFA) 1.20–2.20 (7H, m), 4.60–5.60 (3H, m), 8.06 (1H, d, J=10.0Hz), 9.43 (1H, s) |
| —H* | NH$_2$ | –O–CH$_2$–C*(H)(Me)– | 243.5–247.5 (ethanol-methanol) | 1710 | (d$_1$-TFA) 1.30–2.30 (7H, m), 4.70–5.60 (3H, m), 8.05 (1H, d, J=9.5Hz), 9.43 (1H, s) |
| —H | NH$_2$ (Me on cyclopropyl) | –O–CH$_2$–C*(H)(Me)– | 232–236 (6 N hydrochloric acid-ethanol) | 1710 | (d$_1$-TFA) 1.30–2.20 (9H, m), 4.70–5.50 (3H, m), 8.06 (1H, d, J=10.0Hz), 9.41 (1H, s) |
| —H | NH$_2$ | –O–CH$_2$–C*(H)(Et)– | 197–200 (isopropanol) | 1690 | (d$_1$-TFA) 1.00–2.50 (9H, m), 4.70–5.40 (3H, m), 8.05 (1H, d, J=9.5Hz), 9.37 (1H, s) |
| —H | NH$_2$ | –O–CH$_2$–CH(CH$_2$OH)– | 256–259 (6 N hydrochloric acid-ethanol) | 1705 | (d$_6$-DMSO) 1.00–1.80 (4H, m), 4.30–5.20 (5H, m), 7.64 (1H, d, J=10.0Hz), 8.84 (1H, s) |
| —H | NH$_2$ | –O–C(Me)$_2$–CH$_2$– | 242–248 (6 N hydrochloric acid-ethanol) | 1715 | (d$_1$-TFA) 1.30–2.40 (10H, m), 4.74 (2H, bs), 8.08 (1H, d, J=9.0Hz), 9.49 (1H, s) |
| —H | NH$_2$ | –O–CH$_2$–cyclopropyl | 251–254 (6 N hydrochloric acid-ethanol) | 1715 | (d$_1$-TFA) 1.20–2.40 (8H, m), 4.81 (2H, bs), 8.06 (1H, d, J=9.0Hz), 9.07 (1H, s) |

TABLE 8-continued

| R² | R³ | A R⁴ | Melting point (°C.) (solvent used for recrystallization) | IR (KBr) cm⁻¹: $\nu_{C=O}$ | NMR (solvent) δ value: |
|---|---|---|---|---|---|
| —H | NH₂ (cyclopropyl) | —O—Et | 265~270 (6 N hydrochloric acid-ethanol) | 1705 | (d₁-TFA) 1.30-2.20 (4H, m), 4.80-5.40 (4H, m), 8.02 (1H, d, J=10.0Hz), 9.34 (1H, s) |
| —H | NH₂ (cyclopropyl) | —S—Et | 270~275 | 1705 | (d₁-TFA) 1.40-2.30 (4H, m), 3.40-4.00 (2H, m), 4.90-5.50 (2H, m), 8.23 (1H, d, J=9.0Hz), 9.40 (1H, s) |
| —H | NH₂ (cyclopropyl) | MeN(H)—CH(Me)— | 252~256 (6 N hydrochloric acid-ethanol) | 1720 | (d₁-TFA) 1.40-2.40 (7H, m), 3.50-4.30 (5H, m), 4.90-5.50 (1H, m), 7.89 (1H, d, J=10.0Hz), 9.30 (1H, s) |

Note:
*$[\alpha]_D^{25}$ −32.5° (C = 0.5, H₂O)

In 5 ml of acetic acid was dissolved 50 mg of 8-benzylamino-10-cyclopropyl-9-fluoro-3-methyl-7-oxo-2,3-dihydro-7H-pyrido[1,2,3-de][1,4]benzoxazine-6-carboxylic acid. To the resulting solution was added 50 mg of 5% palladium-carbon. The resulting mixture was stirred at room temperature for 1.5 hours at atmospheric pressure in a hydrogen stream. The reaction mixture was filtered. The filtrate was concentrated to dryness under reduced pressure. Ethanol was added to the residue obtained. The resulting crystals were collected by filtration to obtain 19.7 mg (yield: 50.5%) of 8-amino-10-cyclopropyl9-fluoro-3-methyl-7-oxo-2,3-dihydro-7H-pyrido[1,2,3-de][1,4]benzoxazine-6-carboxylic acid. Melting point: >280° C. (recrystallized from chloroform-ethanol)

IR (KBr) cm⁻¹: $\nu_{C=O}$ 1705

NMR (d₁-TFA) δ value: 1.10-2.00 (7H, m), 2.10-2.60 (1H, m), 4.30-5.40 (3H, m), 9.32 (1H, s).

The following compound was obtained in the same manner:

10-Cyclopropyl-9-fluoro-8-hydroxy-3-methyl-7-oxo-2,3-dihydro-7H-pyrido[1,2,3-de][1,4]benzoxazine-6-carboxylic acid Melting point: 262°-263° C. (recrystallized from ethanol)

IR (KBr) cm⁻¹: $\nu_{C=O}$ 1720

NMR (d₆-DMSO) δ value: 0.90-1.60 (7H, m), 1.80-2.40 (1H, m), 4.20-5.20 (3H, m), 8.93 (1H, s).

EXAMPLE 19 2.5 ml of 6N hydrochloric acid was added to 90 mg of ethyl (S)-10-[1-(N-acetyl-N-methylamino)cyclopropyl]-9-fluoro-3-methyl-7-oxo-2,3-dihydro-7H-pyrido[1,2,3-de][1,4]benzoxazine-6-carboxylate. The resulting mixture was refluxed for 4 hours. The reaction mixture was concentrated under reduced pressure. Ethanol was added to the residue obtained. The resulting crystals were collected by filtration to obtain 50 mg (yield: 62.5%) of (S)-10-(1-methylaminocyclopropyl)-9-fluoro-3-methyl-7-oxo-2,3-dihydro-7H-pyrido[1,2,3-de][1,4]benzoxazine-6-carboxylic acid hydrochloride.

Melting point: 240°-244° C. (recrystallized from 6 N hydrochloric acid-ethanol)

IR (KBr) cm⁻¹: $\nu_{C=O}$ 1720

NMR (d₁-TFA) δ value: 1.30-2.20 (7H, m), 3.03 (3H, s), 4.70-5.50 (3H, m), 8.10 (1H, d, J=10.0 Hz), 9.46 (1H, s).

The compounds shown in Table 9 were obtained in the same manner.

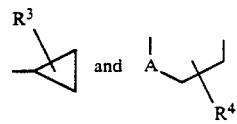

in Table 9 correspond to those in the following formula:

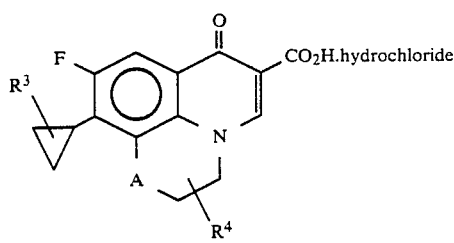

TABLE 9

| R³ (structure) | A-R⁴ (structure) | Melting point (°C.) (solvent used for recrystallization) | IR (KBr) cm⁻¹: νC=O | NMR (d₁-TFA) δ value: |
|---|---|---|---|---|
|  NMe₂ | 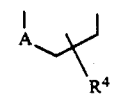 O—Me, H | 260~263 (6 N hydrochloric acid-ethanol) | 1720 | 1.40–2.30 (7H, m), 3.19 (6H, s), 4.70–5.50 (3H, m), 8.14 (1H, d, J=10.0Hz), 9.49 (1H, s) |
|  NH₂ | 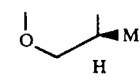 O—Me, H | 186~190 (6 N hydrochloric acid-ethanol) | 1710 | 1.30–2.60 (7H, m), 3.10–3.80 (2H, m), 4.60–5.50 (3H, m), 7.98 (1H, d, J=10.0Hz), 9.32 (1H, s) |
|  NH₂ | 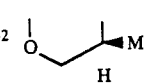 O—F | 243~249 (6 N hydrochloric acid-ethanol) | 1705 | 1.30–2.30 (4H, m), 4.40–5.80 (5H, m), 8.08 (1H, d, J=9.5Hz), 9.39 (1H, s) |

EXAMPLE 20

To 0.5 ml of a 30% hydrogen bromide-acetic acid solution was added with ice-cooling, 50 mg of (S)-10-(2-benzyloxycarbonylaminocyclopropyl)-9-fluoro-3-methyl-7-oxo-2,3-dihydro-7H-pyrido[1,2,3-de][1,4]benzoxazine-6-carboxylic acid. The resulting mixture was stirred at the same temperature for 1 hour. The reaction mixture was concentrated under reduced pressure. To the residue obtained were added 5 ml of chloroform and 5 ml of water in this order. The aqueous layer was separated. The solvent was removed by distillation under reduced pressure. Diethyl ether was added to the residue obtained and the resulting crystals were collected by filtration to obtain 30 mg (yield: 68.2%) of (S)-10-(2-aminocyclopropyl)-9-fluoro-3-methyl-7-oxo-2,3-dihydro-7H-pyrido[1,2,3-de][1,4]benzoxazine-6-carboxylic acid hydrobromide.

Melting point: 245°–250° C. (recrystallized from ethanol)

IR (KBr) cm⁻¹: $\nu_{C=O}$ 1700

NMR (d₁-TFA) δ value: 1.10–2.30 (5H, m), 2.80–3.40 (1H, m), 3.50–4.10 (1H, m), 4.40–5.50 (3H, m), 7.98 (1H, d, J=10.0 Hz), 9.40 (1H, s).

The following compound was obtained in the same manner:

(S)-10-(2-aminocyclopropyl)-9-fluoro-3-methylene-7-oxo-2,3-dihydro-7H-pyrido[1,2,3-de][1,4]benzoxazine-6-carboxylic acid hydrobromide Melting point: 270°–275° C. (recrystallized from ethanol-methanol)

IR (KBr) cm⁻¹: $\nu_{C=O}$ 1705

NMR (d₁-TFA) δ value: 1.30–2.30 (4H, m), 5.34 (2H, s), 5.95 (1H, d, J=4.5 Hz), 6.28 (1H, d, J=4.5 Hz), 8.04 (1H, d, J=9.5 Hz), 9.55 (1H, s).

EXAMPLE 21

In 8.57 ml of water was dissolved 730 mg of (S)-10-(1-aminocyclopropyl)-9-fluoro-3-methyl-7-oxo-2,3-dihydro-7H-pyrido[1,2,3-de][1,4]benzoxazine-6-carboxylic acid hydrochloride, and to the resulting solution were added 242 mg of potassium hydroxide and 5.84 ml of ethanol in this order. Subsequently, 0.19 ml of conc. hydrochloric acid was dropped thereinto at 60° C. in 30 minutes, and thereafter, the resulting mixture was cooled to 20° C. in 2 hours. The mixture was stirred at 20° C. for a further 30 minutes, and the resulting crystals were collected by filtration to obtain 570 mg (yield: 87.0%) of (S)-10-(1-aminocyclopropyl)-9-fluoro-3-methyl-7-oxo-2,3-dihydro-7H-pyrido[1,2,3-de][1,4]benzoxazine-6-carboxylic acid.

Melting point: 269°–271.5° C.

IR (KBr) cm⁻¹: $\nu_{C=O}$ 1705

NMR (d₁-TFA) δ value: 1.30–2.20 (7H, m), 4.45–5.55 (3H, m), 8.06 (1H, d, J=9.5 Hz), 9.42 (1H, s).

$[\Delta]_D^{25}$ −88.0 (C=0.5, 0.05N aqueous sodium hydroxide solution).

EXAMPLE 22

In 120 ml of ethanol was suspended 3.00 g of (S)-10-(1-aminocyclopropyl)-9-fluoro-3-methyl-7-oxo-2,3-dihydro-7H-pyrido[1,2,3-de][1,4]benzoxazine-6-carboxylic acid, and to the resulting suspension was added 996 mg of methanesulfonic acid at 50° C. The resulting mixture was cooled to 20° C. in 2 hours and the resulting crystals were collected by filtration to obtain 3.05 g (yield: 78.1%) of a methanesulfonic acid salt of (S)-10-(1-aminocyclopropyl)-9-fluoro-3-methyl-7-oxo-2,3-dihydro-7H-pyrido[1,2,3-de][1,4]benzoxazine-6-carboxylic acid.

Melting point: 263°–265° C.

IR (KBr) cm⁻¹: $\nu_{C=O}$ 1710

NMR (D₂O) δ value: 1.30–1.90 (7H, m), 2.84 (3H, s), 4.25–5.20 (3H, m), 7.53 (1H, d, J=10.0 Hz), 8.84 (1H, s).

PREPARATION EXAMPLE 1

With 50 g of (S)-10-(1-aminocyclopropyl)-9-fluoro-3-methyl-7-oxo-2,3-dihydro-7H-pyrido[1,2,3-de][1,4]benzoxazine-6-carboxylic acid hydrochloride were blended 49 g of crystalline cellulose, 50 g of corn starch and 1 g of magnesium stearate, and the blend was compressed into 1,000 flat-type tablets.

PREPARATION EXAMPLE 2

50 g of corn starch was blended with 100 g of (S)-10-(1-aminocyclopropyl)-9-fluoro-3-methyl-7-oxo-2,3-dihydro-7H-pyrido[1,2,3-de][1,4]benzoxazine-6-carboxylic acid hydrochloride, and 1,000 capsules were filled with the resulting blend to obtain capsules.

What is claimed is:

1. A pyridone carboxylic acid derivative represented by the following formula or a pharmaceutically acceptable salt thereof:

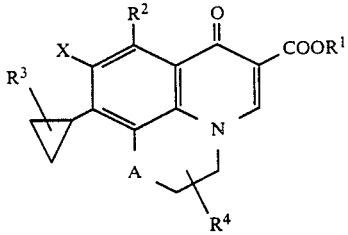

wherein $R^1$ represents a hydrogen atom or a pharmaceutically acceptable carboxyl-protecting group; $R^2$ represents a hydrogen atom, a halogen atom, an alkoxy group, a pharmaceutically acceptable protected or unprotected hydroxyl group, a pharmaceutically acceptable protected or unprotected amino group, a pharmaceutically acceptable protected or unprotected lower alkylamino group or a di-lower alkylamino group; $R^3$ represents at least one group selected from the group consisting of hydrogen atom, lower alkyl group, pharmaceutically acceptable protected or unprotected amino group, pharmaceutically acceptable protected or unprotected lower alkylamino group, di-lower alkylamino group, pharmaceutically acceptable protected or unprotected carboxyl group, pharmaceutically acceptable protected or unprotected amino-lower alkyl group, pharmaceutically acceptable protected or unprotected lower alkylamino-lower alkyl group, di-lower alkylamino-lower alkyl group and pharmaceutically acceptable protected or unprotected hydroxy-lower alkyl group; $R^4$ represents at least one group selected from the group consisting of hydrogen atom, lower alkyl group, halogeno-lower alkyl group, pharmaceutically acceptable protected or unprotected hydroxyl-lower alkyl group, lower alkylidene group and a group forming a cycloalkane ring with the carbon atom to which $R^4$ bonds; X represents a halogen atom; and A represents an oxygen or sulfur atom of a lower alkyl-substituted or unsubstituted imino group.

2. The pyridone carboxylic acid derivative or a pharmaceutically acceptable salt thereof according to claim 1, wherein $R^2$ represents a hydrogen or halogen atom, a pharmaceutically acceptable protected or unprotected hydroxyl group or a pharmaceutically acceptable protected or unprotected amino group; and $R^3$ represents at least one group selected from the group consisting of hydrogen atom, lower alkyl group, pharmaceutically acceptable protected or unprotected amino group, pharmaceutically acceptable protected or unprotected lower alkylamino group, di-lower alkylamino group, pharmaceutically acceptable protected or unprotected carboxyl group and pharmaceutically acceptable protected or unprotected amino-lower alkyl group.

3. The pyridone carboxylic acid derivative or a pharmaceutically acceptable salt thereof according to claim 1, wherein $R^3$ represents at least one group selected from the group consisting of lower alkyl group, pharmaceutically acceptable protected or unprotected amino group and a pharmaceutically acceptable protected or unprotected lower alkylamino group.

4. The pyridone carboxylic acid derivativve or a pharmaceutically acceptable salt thereof according to claim 1, wherein $R^4$ represents at least one group selected from the group consisting of lower alkyl group, halogeno-lower alkyl group, lower alkylidene group and a group forming a cycloalkane ring with the carbon atom to which $R^4$ bonds.

5. The pyridone carboxylic acid or a pharmaceutically acceptable salt thereof according to claim 1, wherein $R^3$ represents a hydrogen atom or a pharmaceutically acceptable protected or unprotected amino group which is bonded to the 1-position of the cyclopropyl group; $R^4$ represents a hydrogen atom or a lower alkyl group; and A represents an oxygen or sulfur atom.

6. The pyridone carboxylic acid derivative or a pharmaceutically acceptable salt thereof according to claim 1, wherein $R^2$ represents a hydrogen atom, a halogen atom, a pharmaceutically acceptable protected or unprotected hydroxyl group or a pharmaceutically acceptable protected or unprotected amino group.

7. The pyridone carboxylic acid derivative or a pharmaceutically acceptable salt thereof according to claim 1, wherein $R^1$ represents a hydrogen atom.

8. The pyridone carboxylic acid derivative or a pharmaceutically acceptable salt thereof according to claim 1, wherein A represents an oxygen atom.

9. The pyridone carboxylic acid derivative or a pharmaceutically acceptable salt thereof according to claim 1, wherein X represents a fluorine atom.

10. 10-(1-Aminocyclopropyl)-9-fluoro-3-methyl-7-oxo-2,3-dihydro-7H-pyrido[1,2,3-de][1,4]benzoxazine-6-carboxylic acid or a pharmaceutically acceptable salt thereof.

11. 8-Amino-10-(1-aminocyclopropyl)-9-fluoro-3-methyl-7-oxo-2,3-dihydro-7H-pyrido[1,2,3-de][1,4]-benzoxazine-6-carboxylic acid or a pharmaceutically acceptable salt thereof.

12. 10-(1-Aminocyclopropyl)-8,9-difluoro-3-methyl-7-oxo-2,3-dihydro-7H-pyrido[1,2,3-de][1,4]benzoxazine-6-carboxylic acid or a pharmaceutically acceptable salt thereof.

13. 10-(1-Aminocyclopropyl)-9-fluoro-8-hydroxy-3-methyl-7-oxo-2,3-dihydro-7H-pyrido[1,2,3-de][1,4]benzoxazine-6-carboxylic acid or a pharmaceutically acceptable salt thereof.

14. (s)-10-(1-aminocyclopropyl)-9-fluoro-3-methyl-7-oxo-2,3-dihydro-7H-pyrido[1,2,3-de][1,4]benzoxazine-6-carboxylic acid or a pharmaceutically acceptable salt thereof.

15. 10-(1-Aminocyclopropyl)-9-fluoro-3-fluoromethyl-7-oxo-2,3-dihydro-7H-pyrido[1,2,3-de][1,4]benzoxazine-6-carboxylic acid or a pharmaceutically acceptable salt thereof.

16. (S)-10-(1-aminocyclopropyl)-3-ethyl-9-fluoro-7-oxo-2,3-dihydro-7H-pyrido[1,2,3-de][1,4]benzoxazine-6-carboxylic acid or a pharmaceutically acceptable salt thereof.

17. 10-(1-Aminocyclopropyl)-9-fluoro-3-methylene-7-oxo-2,3-dihydro-7H-pyrido[1,2,3-de][1,4]benzoxazine-6-carboxylic acid or a pharmaceutically acceptable salt thereof.

18. 10'-(1-Aminocyclopropyl)-9'-fluoro-7'-oxospiro(-cyclopropane-1,3'(2'H)-[7H]-pyrido-[1,2,3-de][1,4]benzoxazine)-6'-carboxylic acid or a pharmaceutically acceptable salt thereof.

19. (S)-10-(1-amino-2-methylcyclopropyl)-9-fluoro-3-methyl-7-oxo-2,3-dihydro-7H-pyrido[1,3,3-de][1,4]-benzoxazine-6-carboxylic acid or a pharmaceutically acceptable salt thereof.

20. (S)-10-[1-(N-methylamino)cyclopropyl]-9-fluoro-3-methyl-7-oxo-2,3-dihydro-7H-pyrido[1,2,3-de][1,4]- benzoxazine-6-carboxylic acid or a pharmaceutically acceptable salt thereof.

21. An antibacterial agent comprising a pyridone carboxylic acid derivative represented by the following formula or a pharmaceutically acceptable salt thereof:

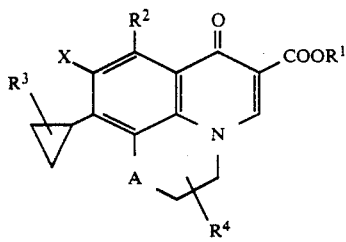

wherein $R^1$ represents a hydrogen atom or a pharmaceutically acceptable carboxyl-protecting group; $R^2$ represents a hydrogen atom, a halogen atom, an alkoxy group, a pharmaceutically acceptable protected or unprotected hydroxyl group, a pharmaceutically acceptable protected or unprotected amino group, a pharmaceutically acceptable protected or unprotected lower alkylamino group or a di-lower alkylamino group; $R^3$ represents at least one group selected from the group consisting of hydrogen atom, lower alkyl group, pharmaceutically acceptable protected or unprotected amino group, pharmaceutically acceptable protected or unprotected lower alkylamino group, di-lower alkylamino group, pharmaceutically acceptable protected or unprotected carboxyl group, pharmaceutically acceptable protected or unprotected amino-lower alkyl group, pharmaceutically acceptable protected or unprotected lower alkylamino-lower alkyl group, di-lower alkylaminolower alkyl group and a pharmaceutically acceptable protected or unprotected hydroxy-lower alkyl group; $R^4$ represents at least one group selected from the group consisting of hydrogen atom, lower alkyl group, halogeno-lower alkyl group, pharmaceutically acceptable protected or unprotected hydroxyl-lower alkyl group, a lower alkylidene group and a group forming a cycloalkane ring with the carbon atom to which $R^4$ bonds; X represents a halogen atom; and A represents an oxygen or sulfur atom or a lower alkyl-substituted or unsubstituted imino group.

22. The antibacterial agent according to claim 21, wherein $R^2$ represents a hydrogen or halogen atom, a pharmaceutically acceptable protected or unprotected hydroxyl group or a pharmaceutically acceptable protected or unprotected amino group; and $R^3$ represents at least one group selected from the group consisting of hydrogen atom, lower alkyl group, pharmaceutically acceptable protected or unprotected amino group, pharmaceutically acceptable protected or unprotected lower alkylamino group, di-lower alkylamino group, pharmaceutically acceptable protected or unprotected carboxyl group and pharmaceutically acceptable protected or unprotected amino-lower alkyl group.

23. The antibacterial agent according to claim 21, wherein $R^3$ represents at least one group selected from the group consisting of lower alkyl group, pharmaceutically acceptable protected or unprotected amino group and pharmaceutically acceptable protected or unprotected lower alkylamino group.

24. The antibacterial agent according to claim 21, wherein $R^4$ represents at least one group selected from the group consisting of lower alkyl group, halogeno-lower alkyl group, lower alkylidene group and a group which forms a cycloalkane ring with the carbon atom to which $R^4$ bonds.

25. The antibacterial agent according to claim 21, wherein $R^3$ represents a hydrogen atom or a pharmaceutically acceptable protected or unprotected amino group which is bonded to the 1-position of the cyclopropyl group; $R^4$ represents a hydrogen atom or a lower alkyl group; and A represents an oxygen or a sulfur atom.

26. The antibacterial agent according to claim 21 wherein $R^2$ represents a hydrogen atom, a halogen atom, a pharmaceutically acceptable protected or unprotected hydroxyl group or a pharmaceutically acceptable protected or unprotected amino group.

27. The antibacterial agent according to claim 21, wherein Rhu 1 represents a hydrogen atom.

28. The antibacterial agent according to claim 21, wherein A represents an oxygen atom.

29. The antibacterial agent according to claim 21, wherein X represents a fluorine atom.

30. The antibacterial agent, according to claim 21, comprising 10-(1-aminocyclopropyl-9-fluoro-3-methyl-7-oxo-2,3-dihydro-7H-pyrido[1,2,3-de][1,4]benzoxazine-6-carboxylic acid or a pharmaceutically acceptable salt thereof.

31. The antibacterial agent according to claim 21, comprising 8-amino-10-(1-aminocyclopropyl)-9-fluoro-3-methyl-7-oxo-2,3-dihydro-7H-pyrido[1,2,3-de][1,4-]benzoxazine-6-carboxylic acid or a pharmaceutically acceptable salt thereof.

32. The antibacterial agent according to claim 21, comprising 10-(1-aminocyclopropyl)-8,9-difluoro-3-methyl-7-oxo-2,3-dihydro-7H-pyrido[1,2,3-de][1,4]benzoxazine-6-carboxylic acid or a pharmaceutically acceptable salt thereof.

33. The antibacterial agent according to claim 21, comprising 10-(1-aminocyclopropyl)-9-fluoro-8-hydroxy-3- methyl- 7-oxo-2,3-dihydro-7H-pyrido[1,2,3-de][1,4]benzoxazine-6-carboxylic acid or a pharmaceutically acceptable salt thereof.

34. The antibacterial agent according to claim 21, comprising (S)-10-(1-aminocyclopropyl)-9-fluoro-3-methyl-7-oxo-2, 3-dihydro-7H-pyrido[1,2,3-de][1,4]benzoxazine-6-carboxylic acid or a pharmaceutically acceptable salt thereof.

35. The antibacterial agent according to claim 21, comprising 10-(1-aminocyclopropyl)-9-fluoro-3-fluoromethyl-7-oxo-2, 3-dihydro-7H-pyrido[1,2,3-de][1,4]benzoxazine-6-carboxylic acid or a pharmaceutically acceptable salt thereof.

36. The antibacterial agent according to claim 21, comprising (S)-10-(1-aminocyclopropyl)-3-ethyl-9-fluoro-7-oxo-2,3-dihydro-7H-pyrido[1,2,3-de][1,4]benzoxazine-6-carboxylic acid or a pharmaceutically acceptable salt thereof.

37. The antibacterial agent according to claim 21, comprising 10-(1-aminocyclopropyl)-9-fluoro-3-methylene-7-oxo-2, 3-dihydro-7H-pyrido[1,2,3-de][1,4]benzoxazine-6-carboxylic acid or a pharmaceutically acceptable salt thereof.

38. The antibacterial agent according to claim 21, comprising 10'-(1-aminocyclopropyl)-9'-fluoro-7'-oxospiro{cyclopropane-1,3'(2'H)-pyrido[1,2,3-de][1,4]benzoxazine}-6'-carboxylic acid or a pharmaceutically acceptable salt thereof.

39. The antibacterial agent according to claim 21, comprising (S)-10-(1-amino-2-methylcyclopropyl)-9- fluoro-3-methyl-7-oxo-2,3-dihydro-7H-pyrido[1,2,3-de][1,4]-benzoxazine-6-carboxylic acid or a pharmaceutically acceptable salt thereof.

40. The antibacterial agent according to claim 21, comprising (S)-10-[1-(N-methylamino)cyclopropyl]-9-fluoro-3-methyl-7-oxo-2,3-dihydro-7H-pyrido[1,2,3-de][1,4]benzoxazine-6-carboxylic acid or a pharmaceutically acceptable salt thereof.

41. A method of manufacturing a therapeutic agent for treating diseases caused by bacterial infection, which comprises adding one or more inert ingredients to an effective amount of the pyridine carboxylic acid derivative according to claim 1.

42. A method of treating diseases caused by bacterial infection in a mammal, which comprises administering to said mammal a therapeutic agent containing an effective amount of the pyridone carboxylic acid derivative according to claim 1.

43. The pyridone carboxylic acid derivative or a pharmaceutically acceptable salt thereof according to claim 1, wherein $R^3$ represents a pharmaceutically acceptable protected or unprotected amino group, said $R^3$ being bonded to the 1-position of the cyclopropyl group; $R^4$ represents a hydrogen atom or an alkyl group; and A represents a oxygen or sulfur atom.

44. The pyridone carboxylic acid derivative or a pharmaceutically acceptable salt thereof according to claim 43, wherein $R^2$ represents a hydrogen or halogen atom or a hydroxyl or amino group.

45. The pyridone carboxylic acid derivative or a pharmaceutically acceptable salt thereof according to claim 44, wherein $R^3$ represents an amino group.

46. The pyridone carboxylic acid derivative or a pharmaceutically acceptable salt thereof according to claim 45, wherein $R^4$ represents an alkyl group.

47. The pyridone carboxylic acid derivative or a pharmaceutically acceptable salt thereof according to claim 46, wherein A represents an oxygen atom.

48. The pyridone carboxylic acid derivative or a pharmaceutically acceptable salt thereof according to any one of claims 43-47, wherein X represents a fluorine atom.

49. A method of manufacturing a therapeutic agent for treating diseases caused by bacterial infection, which comprises adding one or more inert ingredients to an effective amount of the pyridone carboxylic acid derivative according to claim 43.

50. A method of treating disease caused by bacterial infection in a mammal, which comprises administering to said animal a therapeutic agent containing an effective amount of pyridone carboxylic acid derivative according to claim 43.

* * * * *